(12) United States Patent
Benoit et al.

(10) Patent No.: US 10,302,798 B2
(45) Date of Patent: May 28, 2019

(54) ADVANCED WORKFLOW FOR EVALUATING FORMATION DAMAGE AND STABILIZATION TREATMENTS

(71) Applicant: Halliburton Energy Services, Inc., Houston, TX (US)

(72) Inventors: Denise Nicole Benoit, Houston, TX (US); Antonio Recio, III, Humble, TX (US); Kurt William Hoeman, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 64 days.

(21) Appl. No.: 15/475,744

(22) Filed: Mar. 31, 2017

(65) Prior Publication Data

US 2018/0202957 A1 Jul. 19, 2018

Related U.S. Application Data

(60) Provisional application No. 62/445,863, filed on Jan. 13, 2017.

(51) Int. Cl.
*G01N 15/08* (2006.01)
*E21B 43/26* (2006.01)
(Continued)

(52) U.S. Cl.
CPC .............. *G01V 3/20* (2013.01); *G01N 15/082* (2013.01); *G01N 33/24* (2013.01)

(58) Field of Classification Search
None
See application file for complete search history.

(56) References Cited

U.S. PATENT DOCUMENTS

2010/0270023 A1* 10/2010 Dusterhoft .............. C09K 8/575
166/308.6
2013/0238304 A1* 9/2013 Glinsky .............. G06F 17/5009
703/6
2016/0131628 A1 5/2016 Fontenelle et al.

FOREIGN PATENT DOCUMENTS

WO 2016/072989 A1 5/2016

OTHER PUBLICATIONS

"RockPerm™ Service" Halliburton Energy Services, Inc. Jun. 2015 (3 pages).

(Continued)

*Primary Examiner* — Angela M DiTrani Leff
(74) *Attorney, Agent, or Firm* — Thomas Rooney; Baker Botts L.L.P.

(57) ABSTRACT

Methods of evaluating and/or selecting formation stabilization treatments for subterranean formations are provided. In some embodiments, the methods comprise: subjecting a test formation sample to stress loads, wherein sample comprises: two wafers of a formation material from a subterranean formation, and a plurality of proppant particulates between and in contact with the two wafers; measuring a conductivity of a test fluid through the test formation sample, wherein an eluted test fluid is collected after passing through the test formation sample; determining one or more damage properties of the test formation sample using computed tomography images; determining one or more properties of the eluted test fluid; and selecting a formation stabilization treatment for the subterranean formation based at least in part on the conductivity of the test fluid through the test formation sample, the damage properties of the test formation sample, and/or the properties of the eluted test fluid.

10 Claims, 18 Drawing Sheets

(51) Int. Cl.
G01V 3/20 (2006.01)
G01N 33/24 (2006.01)

(56) References Cited

OTHER PUBLICATIONS

Program for SPE International Conference on Oilfield Chemistry, Apr. 3-5, 2017 (36 pages).
Zhang, Junjing, Ding Zhu, and A. Daniel Hill. "Water-induced damage to propped-fracture conductivity in shale formations." SPE Production & Operations 31, No. 02 (2016): 147-156. (10 pages).
Zhang, Junjing. "Fracture conductivity damage by water in shale formations." Proceedings of the SPE Annual Technical Conference and Exhibition, Amsterdam, The Netherlands, Society of Petroleum Engineers, 2014. (14 pages).
Benoit, Denise, Antonio Recio, Ruslan Gashimov, Dandan Hu, Kristina Holan, and Kurt Hoeman. "In-Depth Analysis of How Chemical Treatments Work to Improve Conductivity in Shale Formations." In SPE International Conference on Oilfield Chemistry. Society of Petroleum Engineers, 2017. (13 pages).
Benoit, Denise, et al. "In-Depth Analysis of How Chemical Treatments Work to Improve Conductivity in Shale Formations." Microsoft Powerpoint presentation, Apr. 2017(16 pages).
Recio, Antonio, Denise Benoit, Kristina Henkel, and Kevin York. "Which Cations are Detrimental to Shale Preservation?" In SPE International Conference on Oilfield Chemistry. Society of Petroleum Engineers, 2017. (17 pages).
Recio, Antonio, et al. "Which Cations are Detrimental to Shale Preservation?" Microsoft Powerpoint presentation, Apr. 2017(16 pages).

* cited by examiner

ADVANCED WORKFLOW FOR EVALUATING FORMATION DAMAGE AND STABILIZATION TREATMENTS

CROSS-REFERENCE TO RELATED APPLICATIONS

The present application claims priority to U.S. Provisional Application Ser. No. 62/445,863 filed on Jan. 13, 2017, entitled "Advanced Formation Stabilization Product Recommendation Workflow," the entire disclosure of which is incorporated herein by reference.

BACKGROUND

The present disclosure relates to systems and methods for treating subterranean formations.

Production of oil and gas from subterranean formations may be hindered by formation damage. Most damage occurs due to introduction of fluids and high pump rates that cause swelling and/or mechanical damage in the formation. Formations are prone to water-sensitivity, which can cause damage through swelling, softening, dissolving, forming precipitates, polymer aggregates, sloughing and/or generating migrating fines. The reaction of water with formation minerals produces damage, including weakening, swelling, dispersion, and flocculation, which could lead to significant loss of fracture conductivity in both primary and secondary fractures. Proppant placed in the formation also may crack, break, or degrade when subjected to closure stresses and fluids in the formation, which may cause similar losses of fracture conductivity. All of these issues can potentially decrease production or induce wellbore damage.

In some formations, clays or fines may already be present or fines may be generated during formation treating activity. In some instances, the formation is stable causing no obstruction to the flow of hydrocarbons through the subterranean formation. However, when the formation is not stable, the minerals can swell and/or fines can migrate through the formation until they become lodged in pore throats, thereby decreasing the permeability of the formation. Various treatment products and methods may be available for treating these issues, although different treatments may vary in efficacy in a given formation depending on the cause and/or mechanism of damage in that formation as well as its fluid sensitivity. Laboratory testing methods have been developed to quantify and ascertain the extent and causes of fluid sensitivity and damage for a formation, including X-ray diffraction (XRD), swelling stability tests (SST), mechanical stabilization tests (MST), cation exchange capacity (CEC), and coreflooding. However, each of these test methods may have certain limitations. For example, XRD may be useful for identifying the crystalline materials within the formation, but it cannot be used to predict all impacts from fluid. SST results may be useful for diagnosing clay-induced swelling damage and determining treatments that protect the formation, but SST is only sensitive to swelling and is unresponsive to other damage mechanisms. CEC may correlate well with various mechanical properties that relate to a diverse set of formation damage mechanisms; however, the method is unable to diagnose the different damage mechanisms and cannot be used to determine the effectiveness of treatments. Coreflood testing is not always possible for certain types of shales having very low permeability (e.g., nanodarcy shales).

BRIEF DESCRIPTION OF THE DRAWINGS

These drawings illustrate certain aspects of some of the embodiments of the present disclosure, and should not be used to limit or define the claims.

Figure 1A:
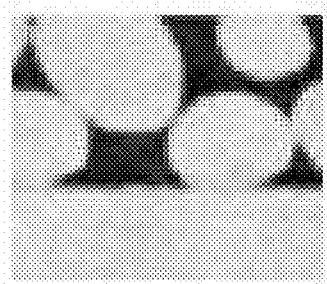
FIGS. 1A, 1B, 1C, 1D, 1E, and 1F are photographic images depicting different degrees of proppant damage and embedment in a formation in certain embodiments of the present disclosure.

While embodiments of this disclosure have been depicted, such embodiments do not imply a limitation on the disclosure, and no such limitation should be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DESCRIPTION OF CERTAIN EMBODIMENTS

The present disclosure relates to systems and methods for treating subterranean formations. More particularly, the present disclosure relates to methods of evaluating and/or selecting formation stabilization treatments for subterranean formations.

The methods and systems of the present disclosure implement a workflow of tests that are used to evaluate the potential causes of damage in a formation to facilitate selection of an effective stabilization treatment for that formation. The methods and systems of the present disclosure use conductivity testing on shale formation wafers subjected to different treatment fluids at increased stress levels to induce damage. The formation-proppant interface is then evaluated using computed tomography (CT) imaging to measure and evaluate damage characteristics of the formation wafers, which may be used to diagnose the internal damage mechanism driving conductivity loss for each formation material in each test fluid. The effluent from the conductivity testing is subjected to water analysis in order to evaluate the geochemical reactions between the formation and components of the fluid. Using the data from each of these tests, one or more formation stabilization treatments effective for addressing the types and causes of damage in the formation may be selected and/or further evaluated (either using this same workflow or a different workflow) and ranked according to their effectiveness in treating or preventing damage. Thus, the methods and systems of the present disclosure may provide improved information relating to: (1) selection criteria for products at simulates reservoir conditions (temperature and pressure); (2) identification of damage prevention (product effects for fracture face stabilization); (3) identification of conductivity enhancements (carbonate dissolution, micro-fracture generation); and (4) ranking of products efficacy, which may facilitate optimal product selection.

In the first stage of the methods of the present disclosure, conductivity testing (e.g., adapted API conductivity cell testing) may be conducted on proppant packs formed between shale formation wafers to quantify the effects of all the fracture materials on the resultant conductivity. In certain embodiments of the conductivity testing, each cell may be composed of two formation material wafers and a layer of proppant placed between the wafers. The wafers are subjected to stress loads of varying magnitude that are sufficient to induce damage on the formation surfaces and/or in the proppant particulates. Tests are run at downhole conditions, including temperature and pressure, with fluids designed for the specific well. After conductivity measurements are obtained, the stress load may be released and the sample wafers may be removed from the cells. The shale wafers with an intact proppant pack are held together for evaluation using CT imaging and the collected effluent fluid is further analyzed.

In some embodiments, micro-CT techniques may use an X-ray source to penetrate the assembled conductivity sample and acquire non-destructive three-dimensional (3D) images of the fluid/rock/proppant system. In these images, the higher density materials such as proppant appear brightest, and the resulting intensities decrease with decreasing density from rock, to fluid, to air (darkest). Each set of 3D CT images may be analyzed over large areas to help determine one or more damage properties of the formation wafers, including but not limited to proppant embedment depth, the extent and size of microfractures in the wafers, percentage of broken proppant, and the like. High-resolution (e.g., 15 μm) images of the fracture face may be acquired and image processing software may be used to segment the materials and diagnose the leading causes of conductivity loss for each sample. Through CT image evaluation, the type of formation damage may categorized, proppant embedment depth may be measured, and percentage of broken proppant may be determined. Additionally, the CT images of the formation wafers can be used to determine the amount of fluid imbibed into the formation and resulting micro-fracture generation (which changes based on imbibition).

In some embodiments, calculation of the proppant embedment depth may include image analysis that provides segmentation of the proppant from formation and then calculation of the peak depth of each proppant. Each proppant-formation interface may be evaluated and scored for the type and extent of damage. An example of a rating scale that may be used to score these evaluations may be structured as follows: 0=no damage, 1=swelling under (not touching), 2=fines under (not touching), 3=slight embedment (<0.5 diameter), 4=significant embedment (>0.5 diameter), and 5=fully engulfed particle and damage beyond (>1 diameter). Table 1 shows examples of ratings and descriptions thereof that may be used in certain embodiments of this analysis, referencing the examples shown in FIGS. 1A through 1F.

TABLE 1

Formation damage factor proppant rating with examples.

Figure 1B:
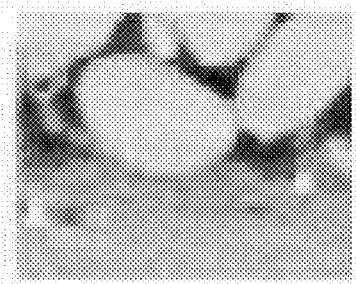
Figure 1C:
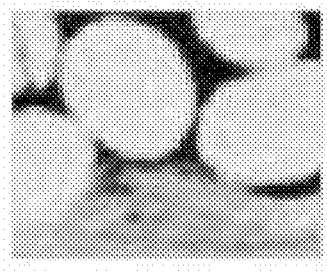
Figure 1D:
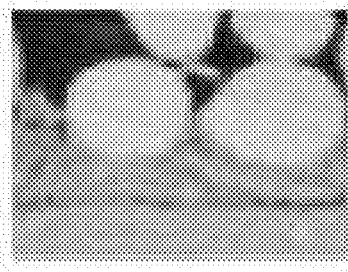
Figure 1E:
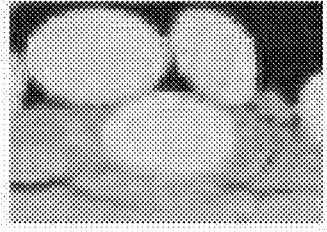
Figure 1F:
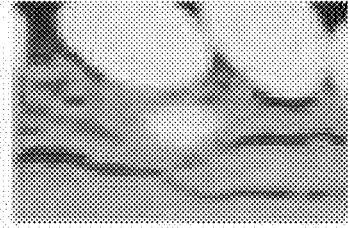

| Rating | Definition | Example |
|---|---|---|
| 0 | No damage | FIG. 1A |
| 1 | Swelling | FIG. 1B |
| 2 | Fines | FIG. 1C |
| 3 | Slight embedment (<0.5 diameter) | FIG. 1D |
| 4 | Significant embedment (>0.5 diameter) | FIG. 1E |
| 5 | Fully engulfed (>1 diameter) | FIG. 1F |

Standard water analysis is also run on all fluids before and after each stress loading during the conductivity testing to monitor geochemical effect of the formation materials due to treatment fluids. One or more properties may be evaluated during this water analysis step, including but not limited to turbidity, mineral dissolution, pH, viscosity, and the like. The role of mineral dissolution has been largely ignored as a formation damaging factor. However, depending on the dissolution amount and interconnected nature of the dissolved mineral the dissolution of carbonates can have a negative or positive impact on the conductivity and damage mechanism. The rate of mineral dissolution may be determined based on the aluminum, calcium, iron, potassium, magnesium, silicon, sodium, carbonates, bicarbonates, chlorides and hydroxide ions in solution. This information may provide evidence of the chemical reactions and kinetics for the formation/fluids, and may be used to diagnose the types of reactions occurring within the fracture network that can either be enhanced for benefit or inhibited for protection. The standard water analysis may include any number of techniques suitable for characterizing and quantifying components in or properties of a fluid, including but not limited to inductively coupled plasma (ICP) analysis, integrated computational element (ICE) analysis, and the like.

Optionally, one or more other methods such as x-ray diffraction (XRD) may be used to determine the formation's mineralogy. In XRD techniques, a diffractometer projects X-ray beams onto finely ground (sub-200-mesh particle size) solid formation material. The crystalline minerals deflect X-rays as they pass through the sample and produce a pattern. The angle of deflection creates defined spacing of peaks. Comparing the patterns to a library of known minerals reveals the composition of crystalline minerals within the formation. The percent of each mineral by weight present in the sample was then calculated based on the relative intensity of the reflections in the test. An example of equipment that may be used to perform XRD analysis is a PANalytical® X'Pert Pro diffractometer.

Figure 14:
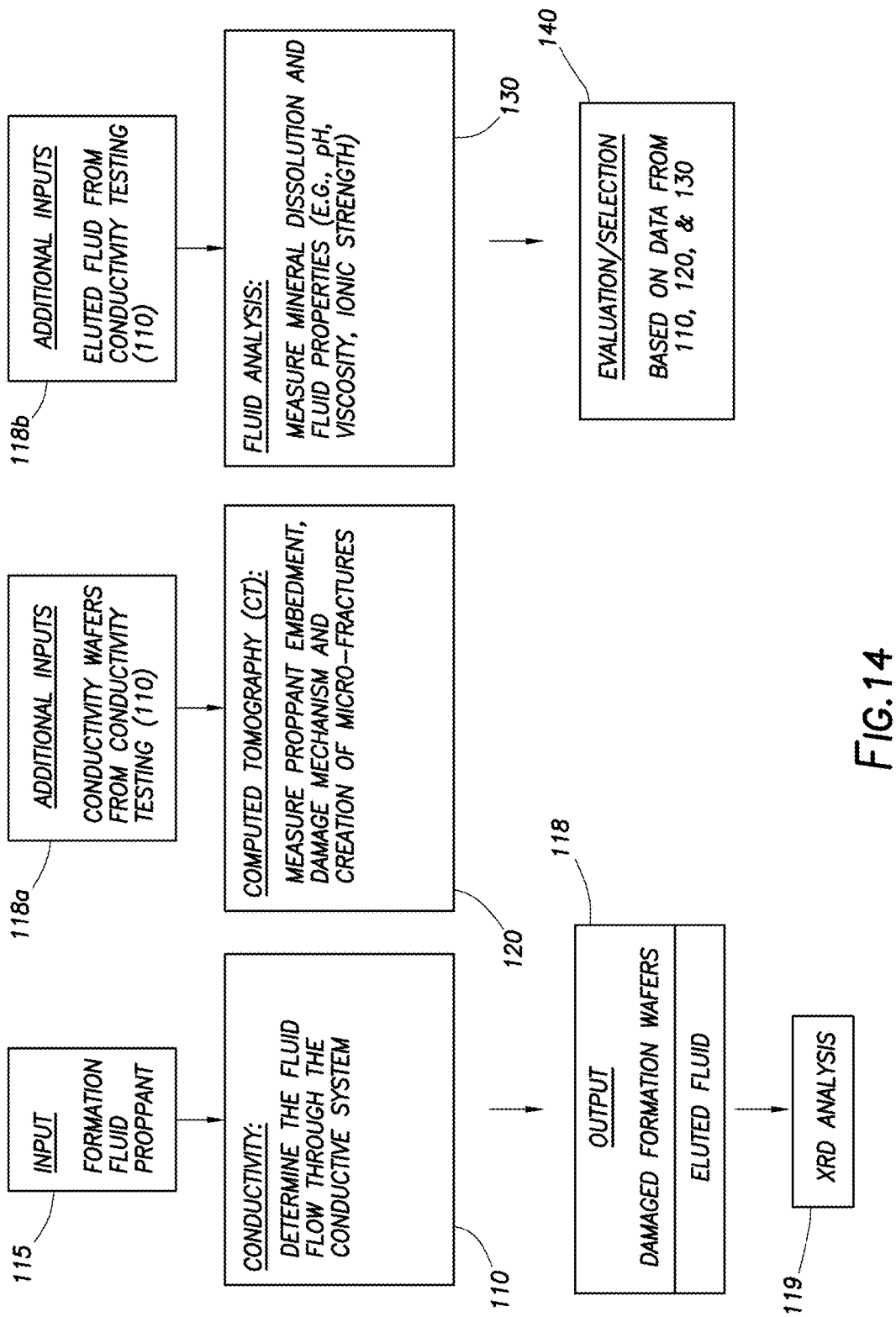
FIG. 14 is a diagram illustrating a workflow for advanced analysis of formation damage.

An analytical workflow 100 as shown in FIG. 14 may be used to evaluate damage in formation materials to help select a suitable treatment product including the appropriate concentration. At step 110, the conductivity of the formation sample may be tested using inputs 115, i.e., the formation material sample wafers, proppant, and fluid (water or a treatment fluid). Outputs 118 from the conductivity testing, i.e., the damaged formation wafers and the eluted fluid, are then collected and used in subsequent steps. Optionally, at step 119, XRD analysis may be performed on the formation materials used in the conductivity step to provide additional information about the formation's composition, mineralogy, etc.

After the conductivity testing in step 110 is complete, computed tomography (CT) images of the formation wafers 118a may be taken at step 120 to visually assess the damage to the formation, measure proppant embedment, measure the amount broken proppant, and assess other damage factors. Also after the conductivity testing of step 110, standard water analysis may be performed at step 130 on the fluid eluted 118b during the conductivity testing at step 110. Steps 120 and 130 may be performed in any order following the conductivity analysis in step 110; in other words, step 120 may be performed before or after step 130, or substantially simultaneously with step 130.

In some embodiments, the fluid used in the conductivity testing of step 110 may be simply fresh water or other fluids already present in the formation (either naturally-occurring or introduced in the course of one or more other treatments). In these embodiments, the data gathered from steps 110, 120 and 130 may be used in the evaluation and/or selection step 140 to evaluate the damage mechanisms in the formation, and select a formation stabilization treatment that is suited to address the damage mechanisms in the formation. In some embodiments, the fluid used in the conductivity testing may comprise one or more additives or treatment products. In these embodiments, the data gathered from steps 110, 120 and 130 may be used in the evaluation and/or selection step 140 wherein the effectiveness of the additive or treatment products is evaluated (e.g., as a percent improvement over the same tests with fresh water or other fluids already present in the formation) or compared with other additives or treatments. Based on this information, a stabilization treatment for the formation may be selected. Optionally, in some embodiments, additional workflows of the present disclosure or other tests may be performed using the stabilization treatment selected at step 140, among other purposes, to select a concentration of the selected stabilization treatment that will be most effective in the formation. Examples of other tests that may be used for this additional step include, but are not limited to swelling stability tests (SST), mechanical stabilization tests (MST), cation exchange capacity (CEC) testing, and the like.

In some embodiments, the data from the conductivity, CT imaging, and/or water analysis tests and the treatments selected using that data may be associated with mineralogy information about the formation obtained from x-ray diffraction or other formation properties, among other reasons, to associate the type of treatment selected with the formation's composition, mineral dissolution characteristics, and/or other properties determined from those steps. This information may be archived or stored, among other purposes, for selecting future treatments for other subterranean formations that have similar characteristics. For example, if a particular treatment was shown to be very effective in mitigating damage in a formation of a particular composition, a user might use that information to select the same treatment for another formation having a similar characteristics. Alternatively, if that treatment was shown to have little or no effect on damage in a formation of another composition, a user can use that information to eliminate possible treatments from those to be evaluated.

Among the many potential advantages to the methods and compositions of the present disclosure, only some of which are alluded to herein, the methods and systems of the present disclosure may allow field lab personnel to use performance based assessments of easy to obtain formation materials with a range of possible treatments to rank their performance and allow for customization of treatment fluids, including (but not limited to) hydraulic fracturing fluids and drilling fluids, based on the chemistry of the particular well. The methods allow lab personnel to demonstrate the water-sensitivity of formations and rank possible treatment options. In some embodiments, the methods and systems of the present disclosure may provide a more direct evaluation of damage in the formation as compared to existing methods and systems, which may facilitate the selection of more effective stabilization treatments for the formation. In some embodiments, the methods and systems of the present disclosure can be used to diagnose fluid/rock compatibilities, fluid/proppant compatibilities, and/or fluid/fluid compatibilities in the formation. In some embodiments, the methods and systems of the present disclosure can be used to diagnose damage prevention and potential benefits to fracture conductivity (in primary and secondary fractures) including imbibition, microfracture generation, and rate of mineral dissolution. In some embodiments, the methods and systems of the present disclosure may help a user recommend an optimal well-specific treatment it increase oil and/or gas production from that well. In some embodiments, the methods and systems of the present disclosure may be able to differentiate the mineral stabilizing characteristics of chemical solutions of the same class (e.g., polymeric, oligomeric, and monomeric quaternary amines), or may be able to differentiate different types of mechanical damage in a formation (e.g., fines generation, sloughing, cracking, and/or other forms of mechanical damage).

Among the damaging minerals that may be present originally in the formation, or may have been introduced therein, are clay materials of the smectite (montmorillonite) group such as montmorillonite, saponite, nontronite, hectorite, beidellite, and sauconite; the kaolin group such as kaolinite, nacrite, dickite, endellite and halloysite; the illite (hydrous-mica) group such as hydrobiotite, glauconite, and illite; the chlorite group (both 7 and 14 angstrom basal spacings) such as chlorite, greenalite and chamosite; clay minerals not belonging to the above groups such as vermiculite, palygorskite (attapulgite) and sepiolite; and mixed-layer (both regular and irregular) varieties of the above minerals. The clay content of the formations can include a single species of a clay mineral or several species, including the mixed-layer types of clay. The clay-containing formations need not be composed entirely of clay, but may contain other mineral components associated therewith. The clays in the formation may be of varying shapes, such as minute, plate-like, tube-like and/or fiber-like particles having an extremely large surface area.

Other types of formation damaging minerals (other than clays) may include any minerals present that will become destabilized due to interaction with the fluids or high pump rates. For example, carbonate minerals in a formation can dissolve when an acidic fluid is introduced into the formation. According to several exemplary embodiments, the subterranean formations include fine-grained, elastic sedimentary rocks composed of different mixtures of clay minerals and other minerals such as quartz, calcite, pyrite, chlorite, feldspar, opal, cristobalite, biotite, clinoptilite, gypsum, and the like. The types of minerals and their morphology in the formation may be of varying shapes and ratios.

The treatment or formation stabilization products evaluated and/or selected using the methods and systems of the present disclosure may comprise any chemical additive that may be used to prevent damage to formation materials in reaction to a water-based fluid and/or non-aqueous based fluids, such as oil, mineral oil, diesel, and condensate. Examples of formation stabilization products that may be used include, but are not limited to, potassium chloride, sodium chloride, ammonium chloride, tetramethyl ammonium chloride, cationic oligomers, cationic polymers, cationic surfactants, hydrophobic resins, transition metals, furfuryl alcohols, ethylene glycol, quaternary amines, bisquaternary amines and the like, as well as any combinations thereof.

The treatment or formation stabilization products evaluated and/or selected using the methods and systems of the present disclosure may be incorporated into a treatment fluid to be introduced (e.g., via one or more pumps or other suitable apparatus) into the subterranean formation to carry out a variety of subterranean treatments, including but not limited to, hydraulic fracturing treatments, acidizing treatments, cleaning treatments, and drilling operations. In hydraulic fracturing treatments, various treatment fluids such as fracturing fluids and/or pre-pad fluids may be used. Hydraulic fracturing has been utilized to stimulate the production of oil, gas and other formation fluids from subterranean formations. In hydraulic fracturing, a suitable fluid is introduced into a subterranean formation by way of a wellbore under conditions of flow rate and pressure, which are at least sufficient to create or enhance one or more fractures into a desired portion of the formation. Fracturing fluid that bleeds into the fracture face often interacts with formation materials and damages permeability of the formation adjacent to the fracture. In certain embodiments of the present disclosure, this damage can be minimized by incorporating the formation stabilization product discussed above into the fracturing fluid at an optimized concentration.

The methods and systems of the present disclosure may be used and/or performed at any stage or location relative to a treating a subterranean formation. For example, in some embodiments, the methods of the present disclosure may be performed (in whole or in part) at a well site where a well bore penetrating the subterranean formation to be treated is located. For example, one or more of the conductivity, CT imaging, and/or water analysis tests may be performed at the well site. In those embodiments, various aspects of the systems of the present disclosure may be designed to be portable and/or readily transportable from one location to another. In other embodiments, one or more portions of the methods of the present disclosure may be performed at an offsite laboratory. In some embodiments, one or more portions of the methods of the present disclosure may be at least partially automated in that they may be performed by a computerized and/or robotic system without human intervention. In some embodiments, one or more components of the systems of the present disclosure may be designed to interface with one or more computer systems whereby data from the various tests and analytical methods described herein may be transmitted to the computer system electronically for display, storage, and/or further analysis.

EXAMPLES

Example 1

Outcrop shale samples were obtained for Barnett (Texas), Eagle Ford (Texas), Mancos (Utah), and Marcellus (Pennsylvania) formations as examples of formations that may be evaluated or treated in accordance with the present disclosure. A workflow according to certain aspects of the methods of the present disclosure using conductivity testing and CT imaging was then used to evaluate damage in fresh water in formation samples from Barnett, Eagle Ford, Mancos, and Marcellus shales.

Fracture Conductivity

Conductivity testing was performed on proppant packs placed between shale formation wafers. All materials were shaped to fit the API conductivity cell (7×1.65×0.5 in.). Silicone was applied to the cores to seal the edges to help prevent flow around the proppant bed. Proppant packs were prepared with 2 lbm/ft² loading of 20/40-mesh, high-crush-resistant ceramic proppant. Each proppant layer was evenly distributed between two shale wafers. During conductivity analysis, four assembled cells were stacked (to reduce total testing time), and closure pressure was applied using a hydraulic press. Measurements were performed at 250° F. (121° C.) over 96 hours. During this time, the materials were allowed to equilibrate at 2,000 psi closure stress and temperature for 48 hours, and then the closure stresses were increased from 2,000 to 10,000 psi in increments of 2,000 psi at 2-hour intervals. Final conductivity measurements were obtained at 10,000 psi after 96 hours at stress. After conductivity measurements were obtained, the stress load was released, and the test samples were carefully removed from the cells. The shale wafers and proppant pack were taped together for evaluation using CT.

For all conductivity measurements, a total of five flow rates were used from 2 to 80 mL/min to exploit the optimal range of the pressure transducers and optimize the data for Forchheimer calculations. To achieve more consistent values, permeability and conductivity were calculated using a combination of Darcy-Forchheimer equations (Eq. 1), where $\Delta p$ is the differential pressure, L is the length, $\nabla p$ is the pressure gradient, $\mu$ is the fluid viscosity, q is the volumetric flow per cross-sectional area, k is the permeability, $\beta$ is the Beta factor (and effective viscosity), and $\rho$ is the fluid density. The pressure gradient was plotted alongside the volumetric flow per cross-sectional area and fitted with a power function to determine $\mu/k$, $\beta\rho$, and the uncertainties in the permeability. The viscosity and density of the fluids were then used to determine permeability and $\beta$ at each confining pressure.

$$\frac{\Delta p}{L} = \nabla p = \frac{\mu}{k}q + \beta\rho q^2 \qquad (1)$$

The fracture width was determined externally using calipers, and the final conductivity calculations were obtained using Eq. 2 where $w_f$ is the fracture width.

$$C = kw_f \qquad (2)$$

Figure 2A:
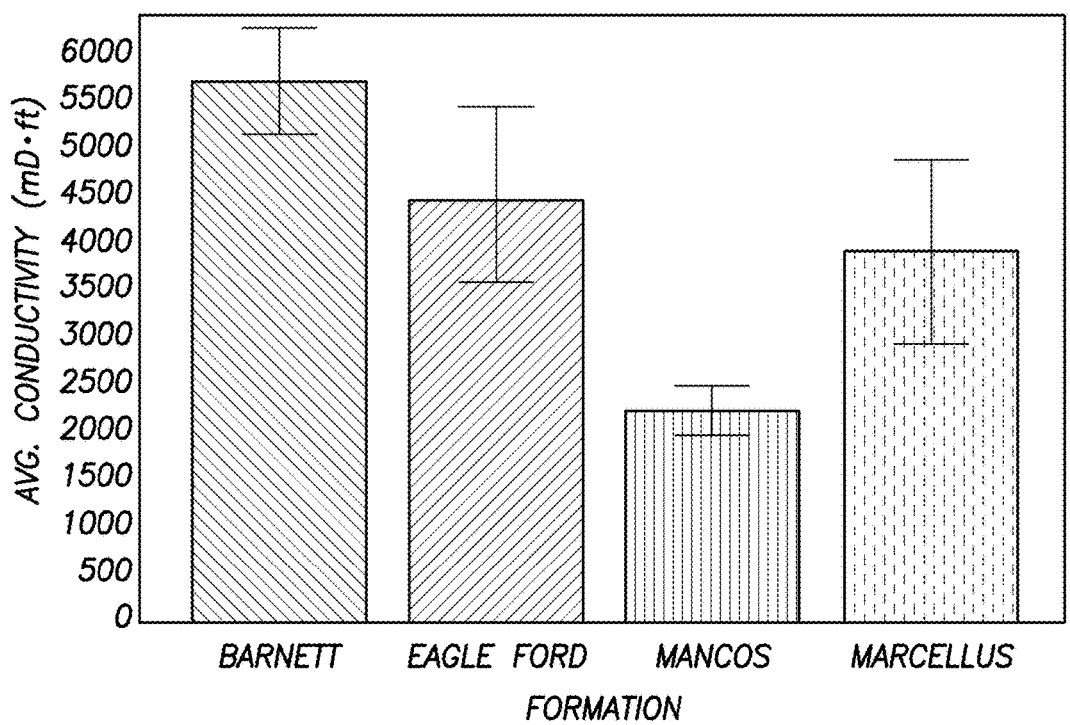
FIGS. 2A, 2B, and 2C are graphs illustrating data regarding conductivity and closure stress in certain formation samples according to certain embodiments of the present disclosure.
Figure 2B:
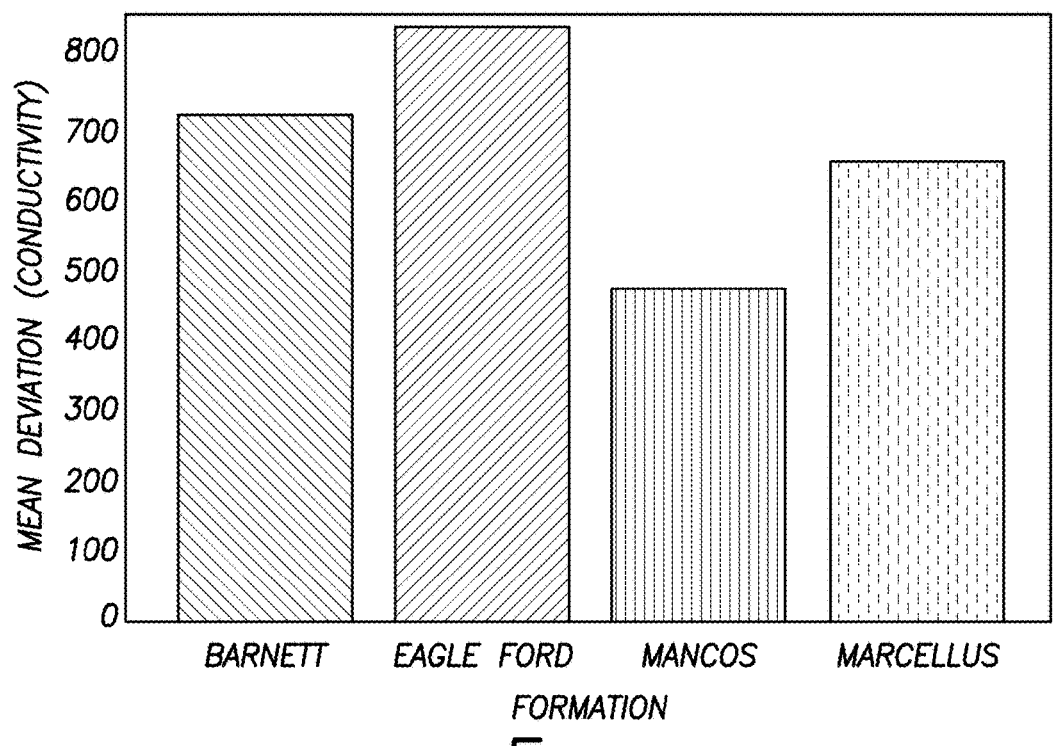
Figure 2C:
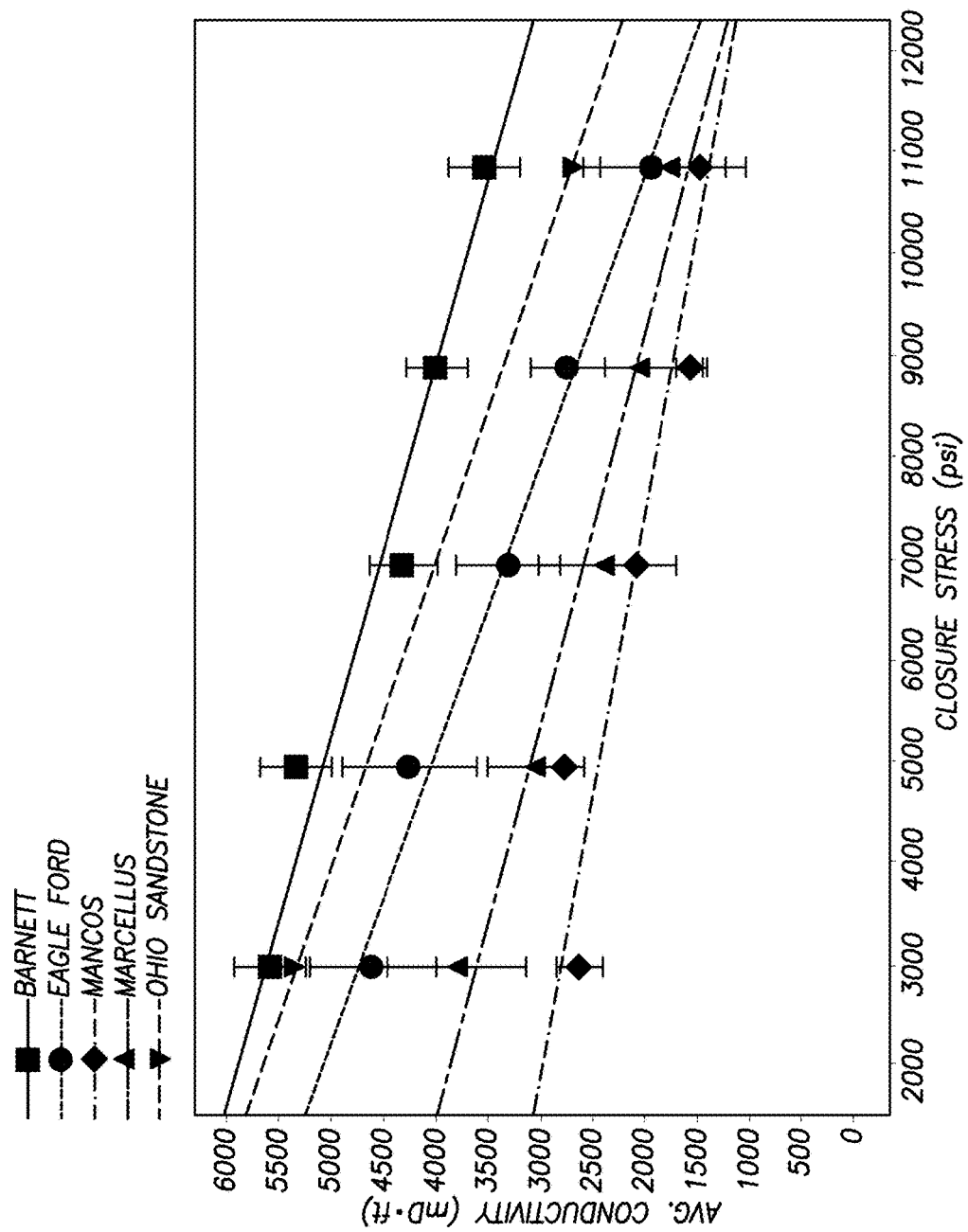

FIGS. 3A and 3B show the average conductivity (using fresh water) for the four shale formations and Ohio sandstone (standard), which is plotted as a function of closure stress in FIG. 3C. Each sample was compared based on initial conductivity and change in conductivity per 1,000 psi increase in closure stress (slope of the lines in FIG. 2). The Ohio sandstone proppant condutivity testing standard showed an initial conductivity of 5337±113 md·ft and a decrease in conductivity of −330 md·ft/1,000 psi. Barnett was the only formation with a higher initial conductivity, 5586±356 md·ft, and lower conductivity loss, −270±30 md·ft/1,000 psi, than the sandstone standard. Eagle Ford exhibited a similar initial conductivity as the standard (4596±605 md·ft), but a higher rate of conductivity loss (−350±30 md·ft/1,000 psi). Marcellus had a lower initial conductivity (3796±664 md·ft) and, compared to Barnett, had a similar stress-induced rate of conductivity loss of −260±30 md·ft/1,000 psi. Mancos had the lowest overall conductivity (2622±223 md·ft) of all samples but was the most resistant to a closure-stress-induced conductivity change, losing only −180±40 md·ft/1,000 psi. Conductivity for each formation sample differed compared to the other formations and compared to the standard sandstone sample. These differences are attributed to the specific formation damage using fresh water test fluid for each sample.

Figure 3:
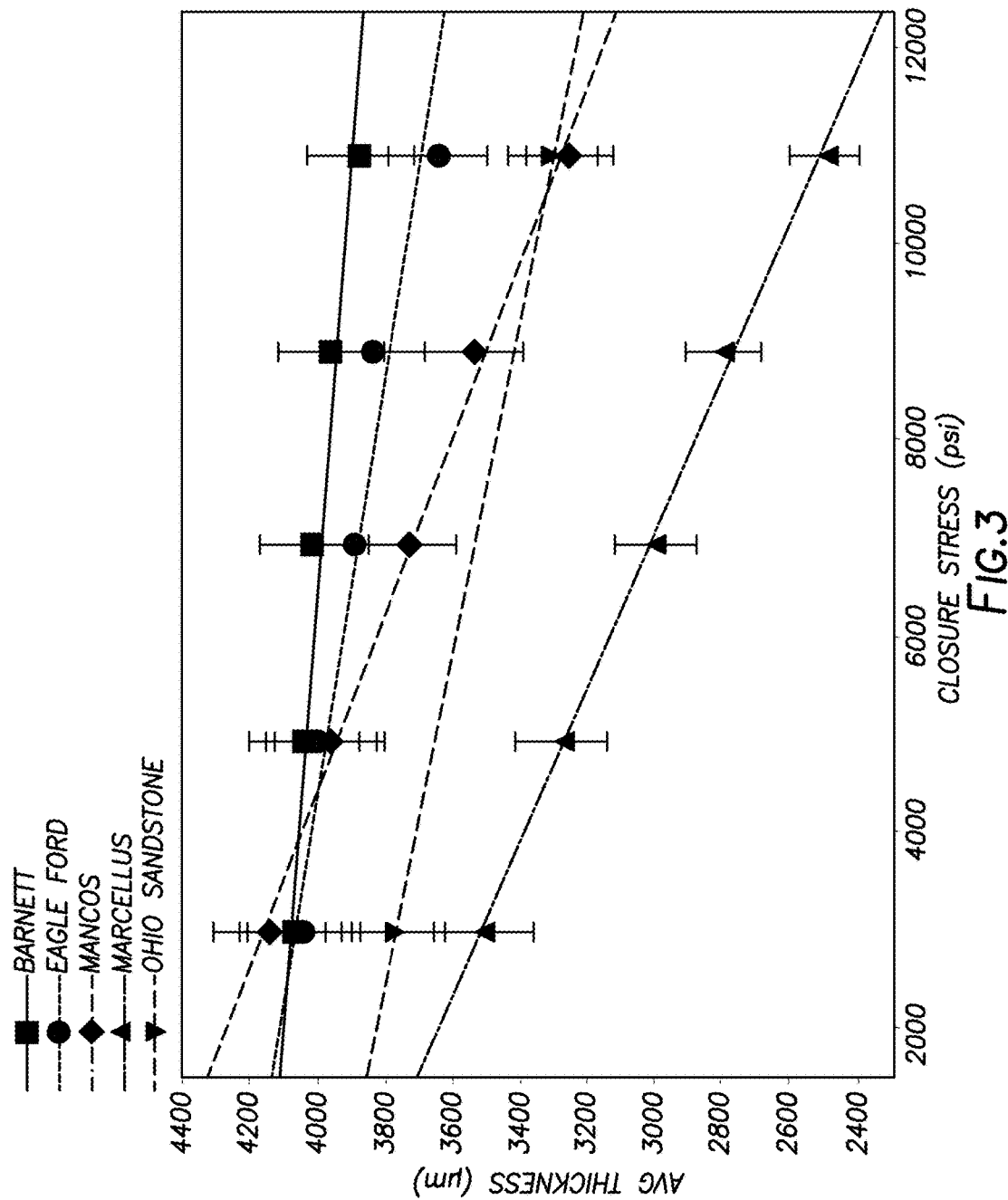
FIG. 3 is a graph illustrating data regarding the effects of closure pressure on fracture width in certain formations according to certain embodiments of the present disclosure.
Figure 4:
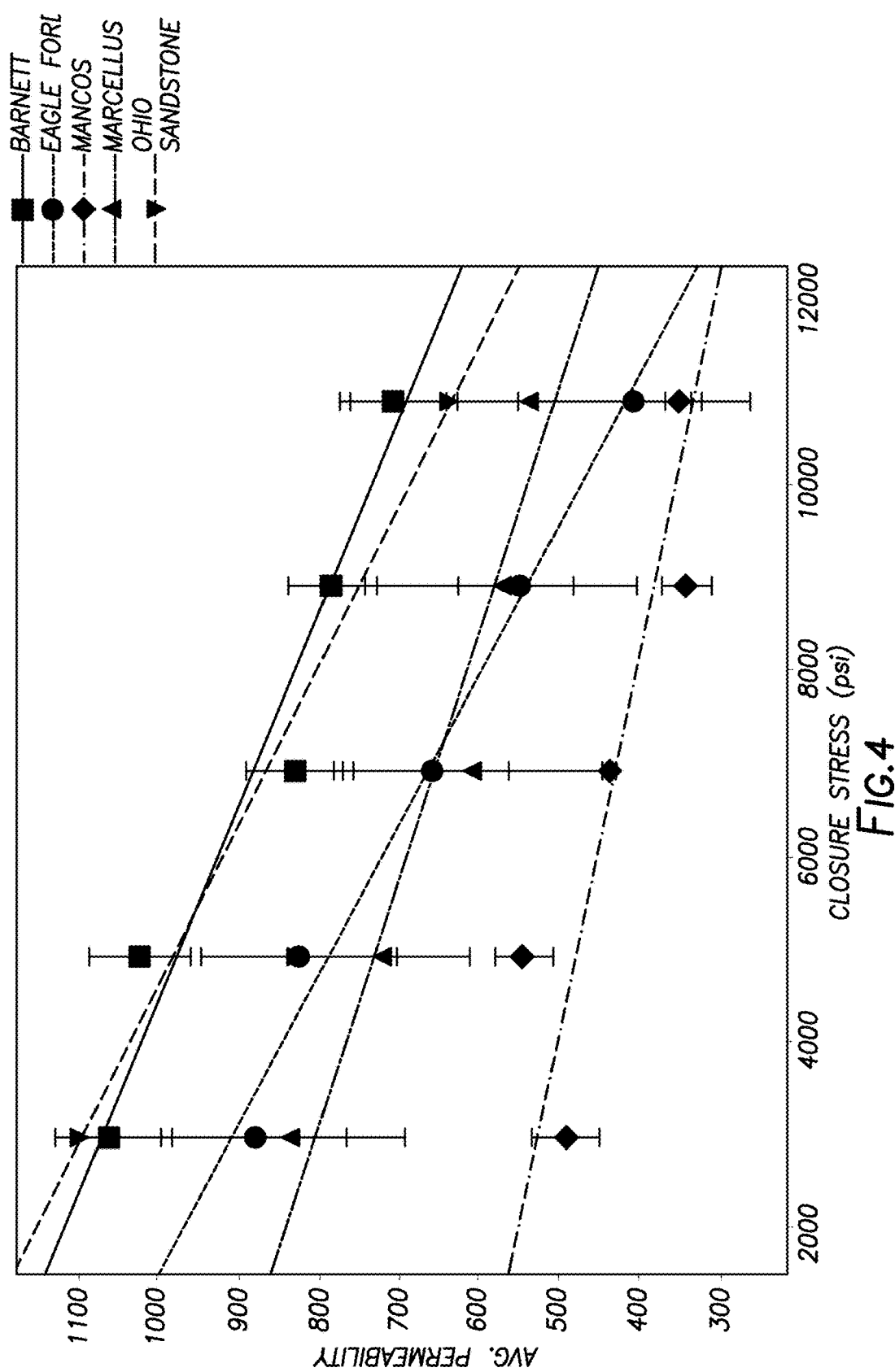
FIG. 4 is a graph illustrating data regarding the effects of closure pressure on permeability in certain formations according to certain embodiments of the present disclosure.

To help determine the mechanism driving the conductivity loss with fresh water resulting from increasing stress specific to each formation, the conductivity calculation was separated into the fracture width and proppant pack permeability, each of which was plotted as a function of closure stress (as shown in FIGS. 3 and 4, respectively). Fracture widths were measured externally using calipers or lasers, while the permeability was calculated based on Darcy's law using pressure gauges along the fracture and measuring the differential pressure response at volumetric flow rates between 2 and 80 mL/min.

For the propped fracture consisting of high-strength proppant packed between Ohio sandstone, the width and permeability reductions for every 1,000 psi were −59 μm and −58 md, respectively. The same proppant with fresh water on Barnett, Eagle Ford, Mancos, or Marcellus shale fractures showed width reductions of −23, −47, −111, and −126 μm/1,000 psi, while permeability reductions were −48, −61, −24, and −37 md/1,000 psi closure pressure, respectively. Two samples, Mancos and Marcellus, showed higher stress-induced changes in thickness, meaning their damage mechanisms would be predominately ones that reduce the fracture width, such as proppant embedment, formation swelling, and proppant breaking. The other two samples, Barnett and Eagle Ford, showed more stress-induced change in the permeability rather than thickness. Comparing Barnett to the sandstone standard shows that the stress-induced decrease in permeability matches closely, indicating that the permeability changes result from the compaction of the proppant pack under stress. The rate of change for Eagle Ford is higher than the standard, indicating there is formation damage that is reducing the permeability, which could include fines generation, proppant breakage, or formation of precipitates. The fracture width and permeability changes were symptoms of the actual formation damage mechanisms responsible for the conductivity loss.

CT Imaging

The formation wafers from the conductivity test were imaged using micro-CT techniques as described above. Proppant embedment, damage factors, percentage of broken proppant, and the damage mechanism was assessed for each formation sample using the micro-CT images and are reported in Table 2 below. The images taken for each of the Barnett, Eagle Ford, Mancos, and Marcellus samples are shown in FIGS. 5A, 5B, 5C, and 5D, respectively. Measurements of more than 500 proppant grains in an area of 1.5×1.5 cm were achieved for every sample, with most samples having ~700 grains at the interface within the analyzed area. Calculating a formation damage factor requires classification of more than 100 proppant grains per sample at intervals of one segment for every 1000 to 1500 μm.

TABLE 2

| CT Image Evaluation | | | | |
| --- | --- | --- | --- | --- |
| | Barnett | Eagle Ford | Mancos | Marcellus |
| Proppant Embedment (μm) | 138 ± 0 | 343 ± 154 | 423 ± 116 | 341 ± 151 |
| Damage Factor | 0.52 | 2.50 | 2.75 | 1.43 |
| Percent broken proppant (%) | 10.5 | 11 | 12.5 | 24 |
| Damage Mechanism | permeability | fines | swelling | proppant breakage |

Figure 5A:
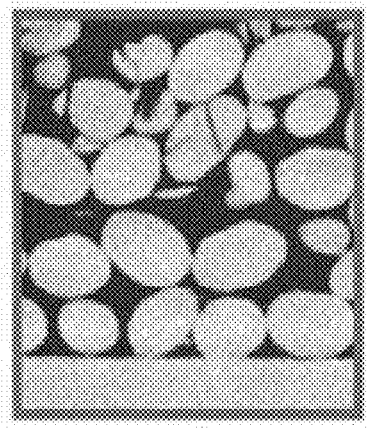
FIGS. 5A, 5B, 5C, and 5D are photographic images depicting proppant embedment and damage in certain treated formation samples according to certain aspects of the present disclosure.
Figure 5B:
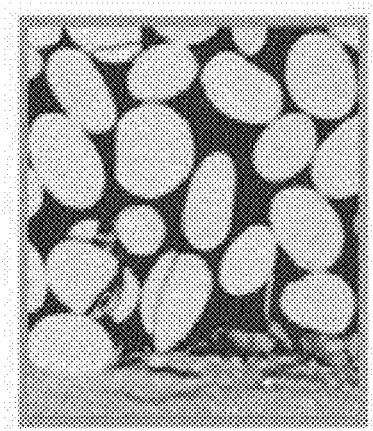
Figure 5C:
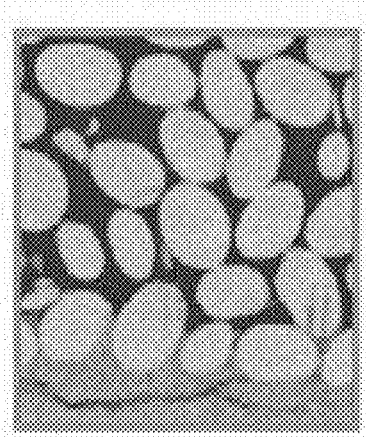
Figure 5D:
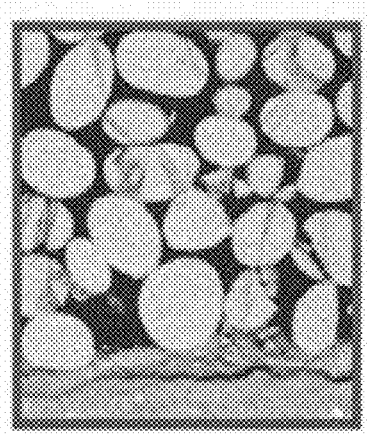

Referring to FIG. 5A, Barnett shows little damage to the fracture face, which was expected because it exhibited the highest conductivity. Analysis of the surface indicated that 55% of the area showed no visible signs of formation damage. Additionally, 38% of the proppant at the interface caused only minor chipping, and 7% of the proppant experienced measurable embedment, averaging 138±1 μm. Referring to FIG. 5B, Eagle Ford showed substantially more spalling resulting from mechanical damage at the interface. Micron-sized fines and spalls were apparent for 95% of the fracture surfaces, and 48% of the proppant at the surface was at least partially embedded, with an average embedment depth of 343±154 μm. Referring to FIG. 5C, Mancos was determined to contain a high percentage of embedded proppant (74%). A total of 10% of the proppants on the surface was fully engulfed, and another 16% were embedded more than half of their diameter; these effects resulted in an average proppant embedment depth of 423±116 μm. Referring to FIG. 5D, Marcellus showed similar mechanical damage and spalling as Eagle Ford; however, only 85% of the total surface showed damage, allowing for more proppants in contact with an undamaged surface. Fewer proppants were embedded, but the average depth was similar, 341±151 μm. Unexpectedly, Marcellus contained a high percentage of broken proppants; 24% of the proppant within the pack was broken or shattered, while each of the other samples contained between 10 and 12% broken proppants.

Full conductivity and CT evaluations of the freshwater propped shale formation materials revealed the differences in damage mechanisms for each formation. Barnett, which exhibited the highest overall conductivity, showed little fluid damage, and the dominate effect on conductivity attributed to stress was decreased permeability in the proppant pack caused by changes in confinement resulting from packing arrangement. Eagle Ford, Mancos, and Marcellus wafers displayed substantially higher fluid-induced formation damage, leading to more significant loss of conductivity under stress. Compared to Barnett and the sandstone standard, Eagle Ford showed a higher stress-induced decrease in permeability resulting from the creation of spalls and fines. Mancos exhibited the lowest conductivity throughout testing and was least affected by the increased stress; the major factor that decreased conductivity was formation swelling, which reduced the fracture width change caused by proppant embedment when stress was increased. Finally, Marcellus exhibited a low conductivity and a large change in fracture width without a substantial amount of proppant embedment; the major damage factors were spalling, fines generation, and proppant breakage.

Example 2

A workflow according to certain aspects of the methods of the present disclosure using conductivity testing and CT imaging was then used to evaluate damage in formation samples from the same four formations (Barnett, Eagle Ford, Mancos, and Marcellus shales) in two potential chemical treatments. The chemical treatments evaluated were a small cationic oligomer additive ("Treatment A") and a large cationic polymer additive ("Treatment B"). Treatment fluids were prepared using fresh water or chemical treatments of 0.1 wt % small cationic oligomer or 0.1 wt % large cationic polymer.

Figure 6A:
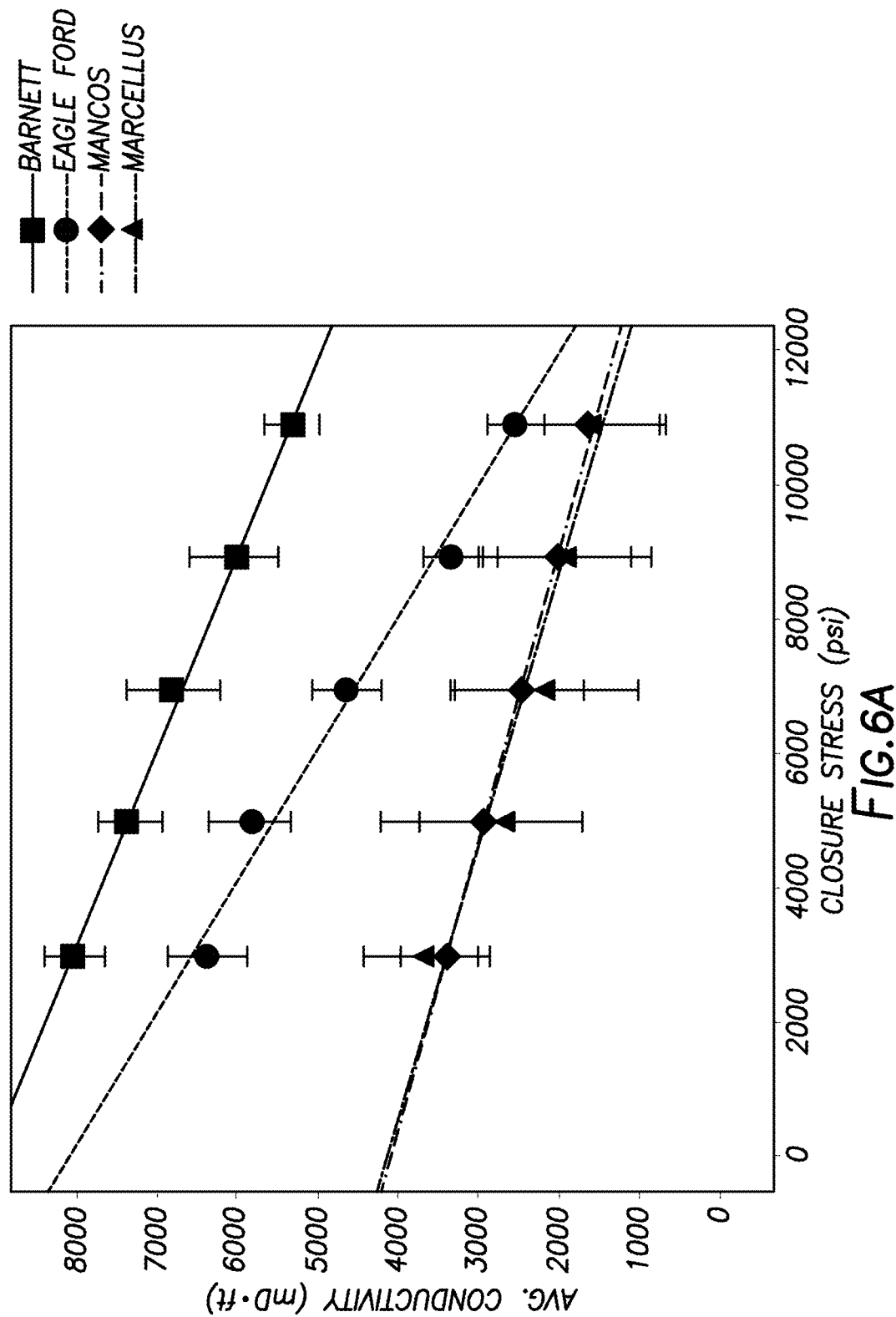
FIGS. 6A and 6B are graphs illustrating data regarding conductivity and closure stress in certain treated formation samples according to certain embodiments of the present disclosure.
Figure 6B:
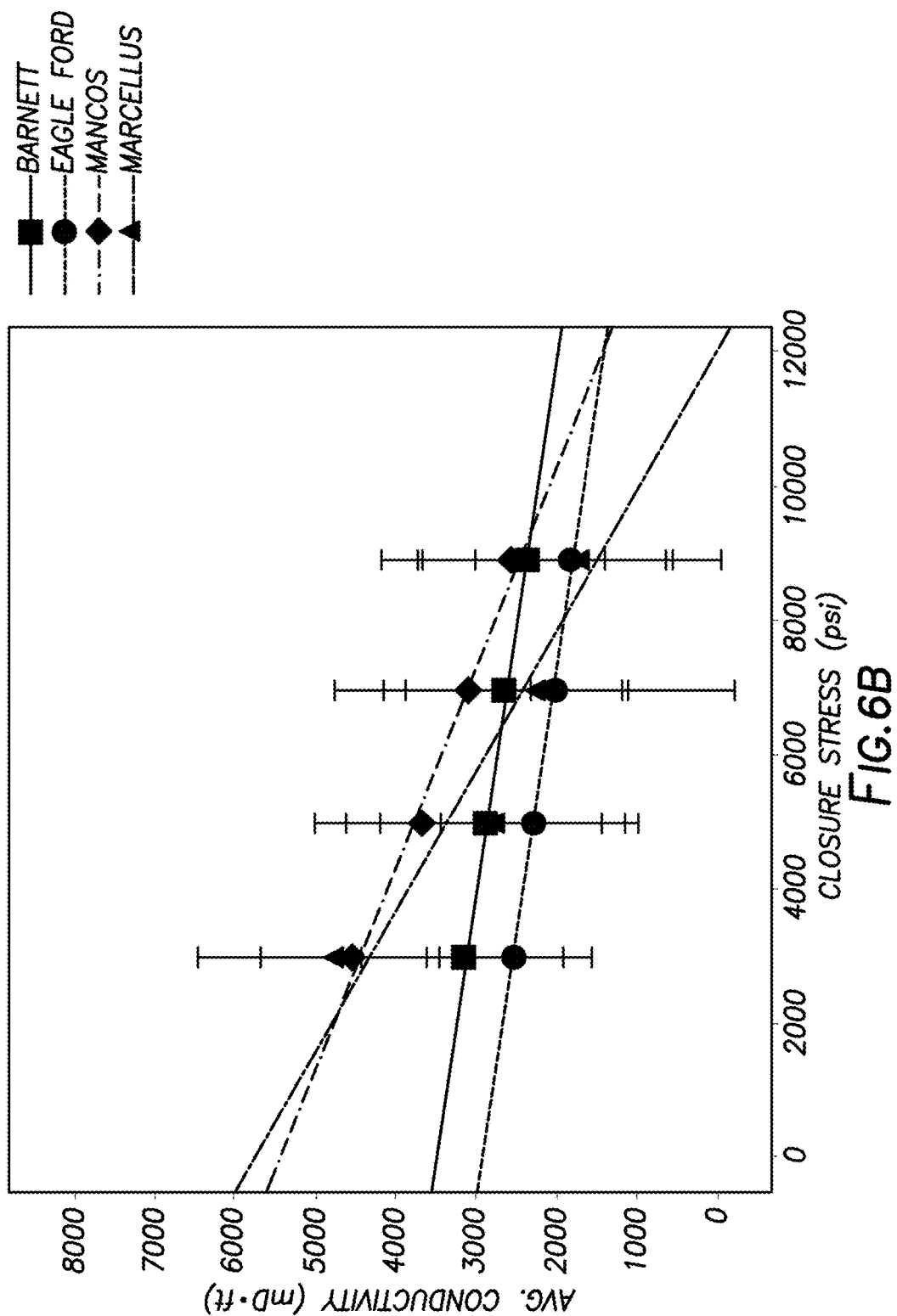
Figure 7A:
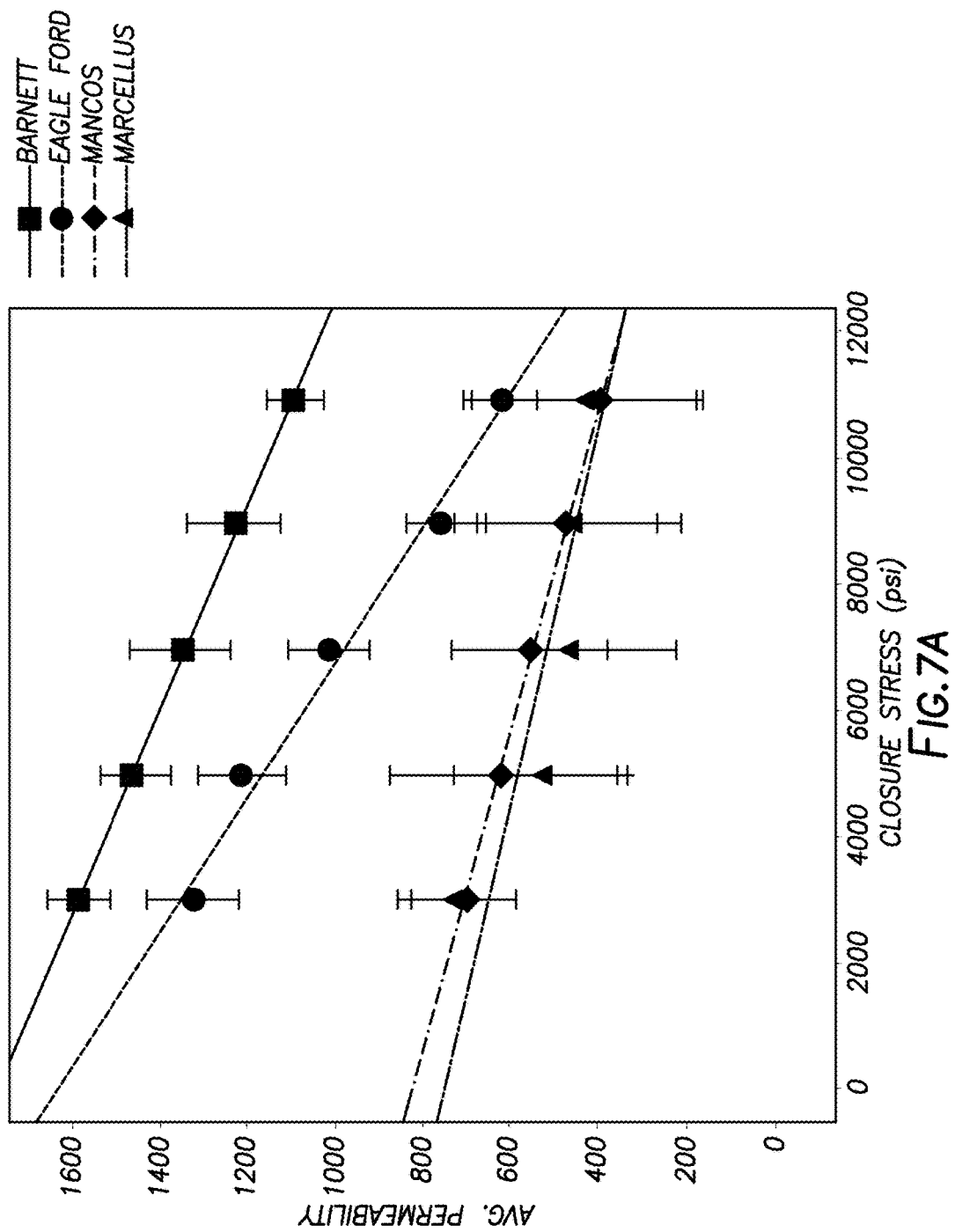
FIGS. 7A and 7B are graphs illustrating data regarding the effects of closure pressure on permeability in certain treated formation samples according to certain embodiments of the present disclosure.
Figure 7B:
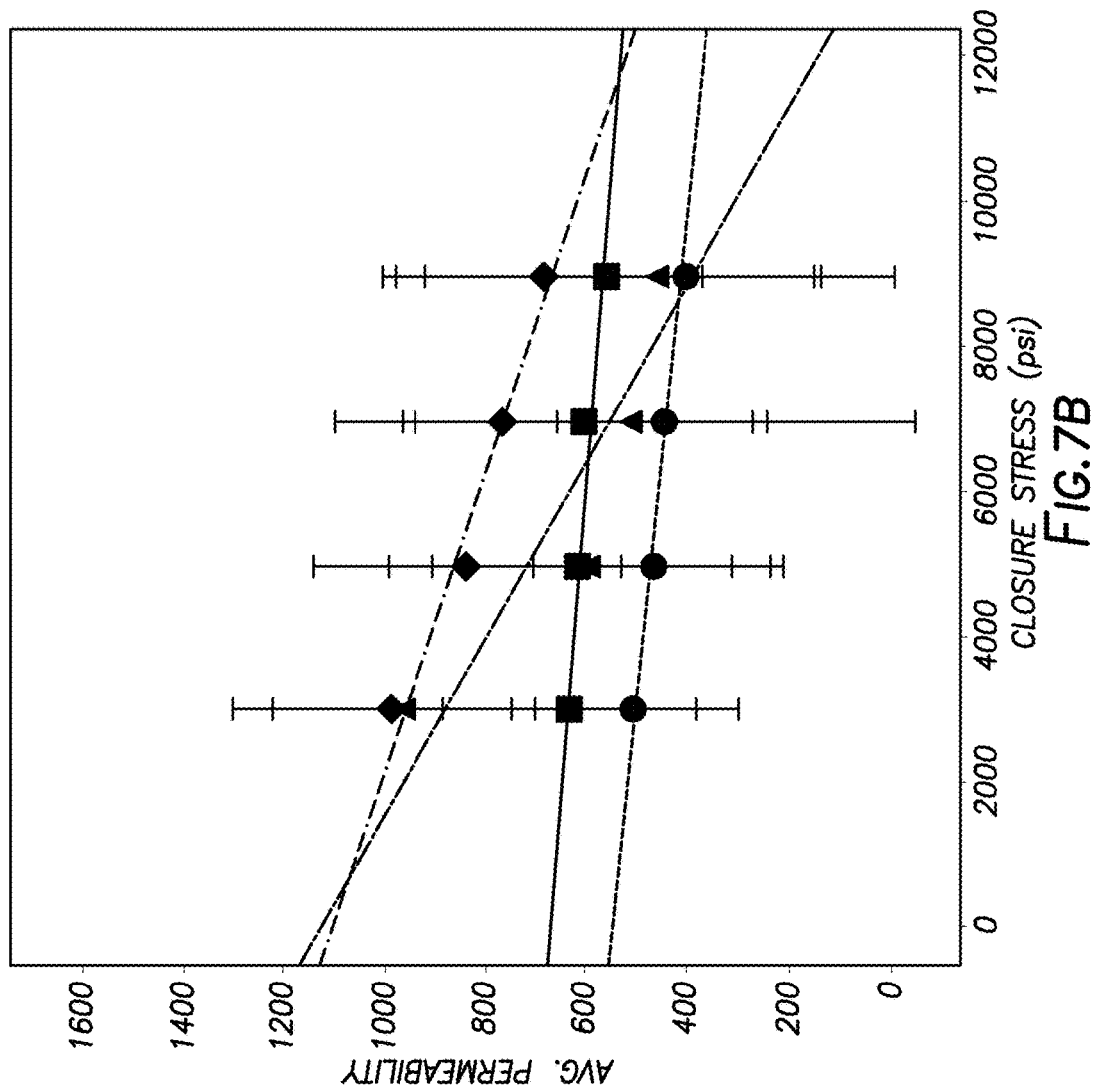
Figure 8A:
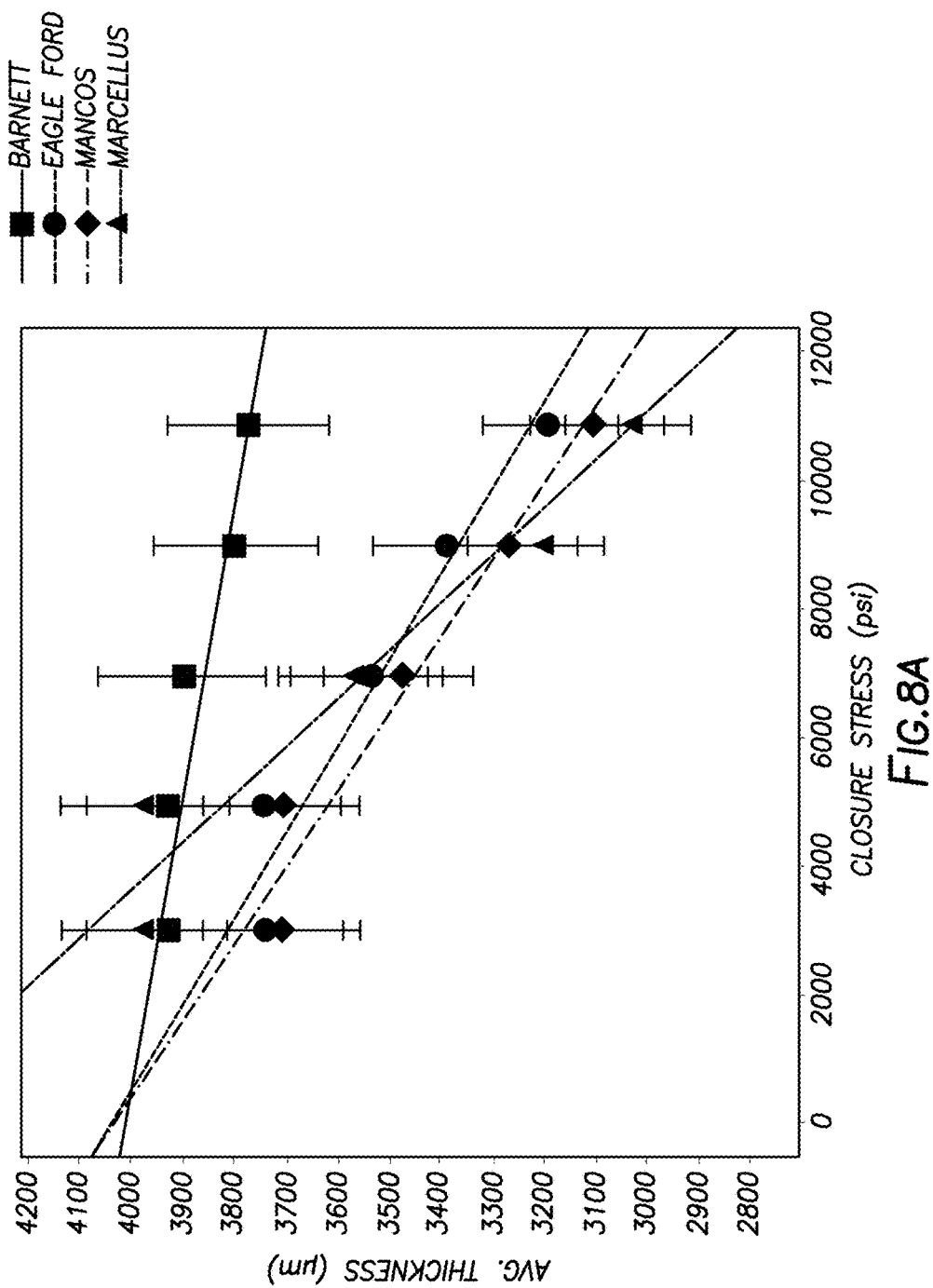
FIGS. 8A and 8B are graphs illustrating data regarding the effects of closure pressure on fracture width in certain treated formation samples according to certain embodiments of the present disclosure.
Figure 8B:
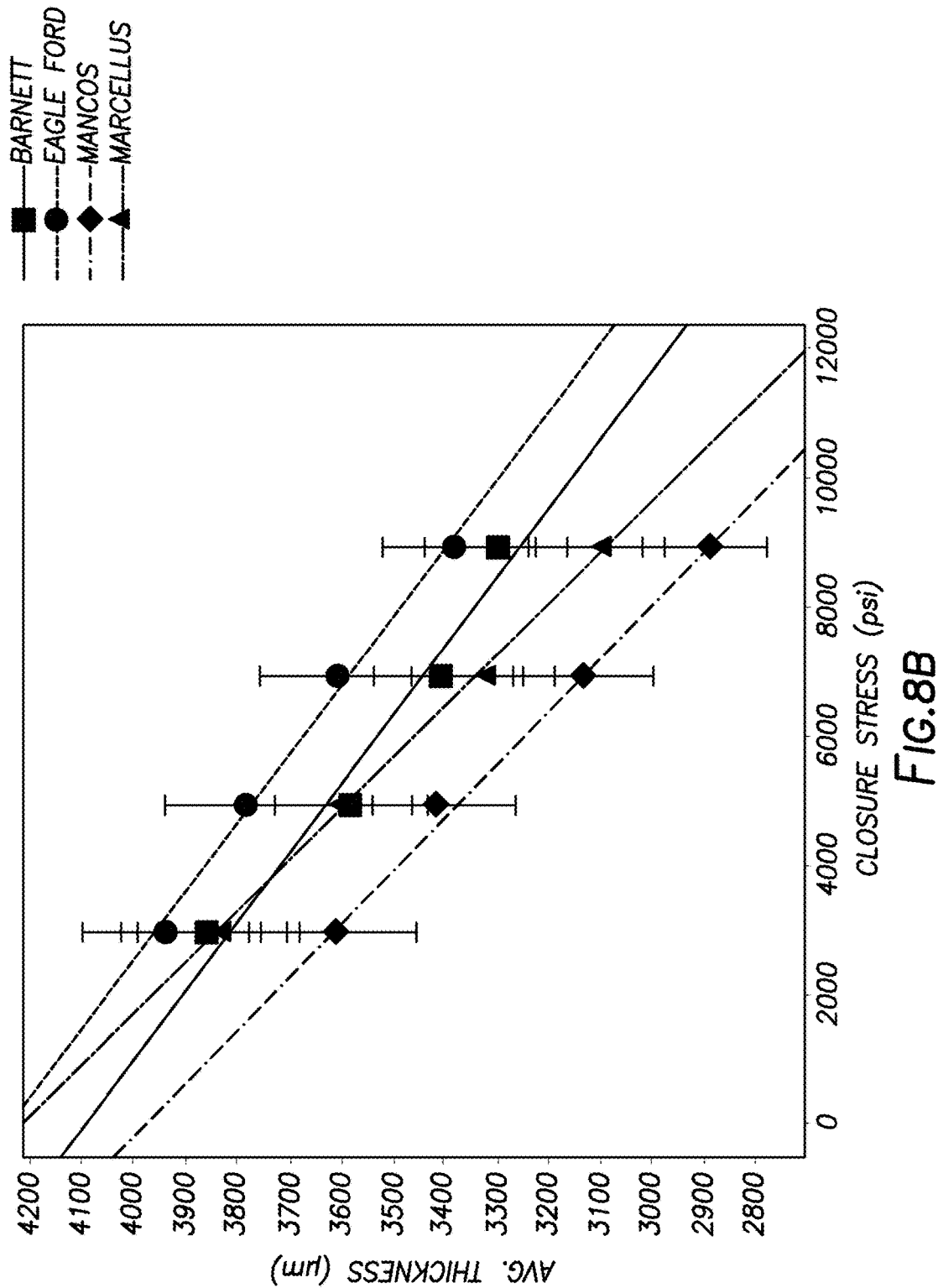

Conductivity testing and calculations performed according to the same procedures described in Example 1 using the treatment fluids instead of freshwater. The conductivities were plotted as a function of closure stress are shown in FIGS. 6A and 6B. The conductivity calculations were also separated into the proppant pack permeability and fracture width and plotted as a function of closure stress, as shown in FIGS. 7A/7B and FIGS. 8A/8B, respectively.

The two shale materials with the highest clay content, Barnett and Mancos, benefited from the addition of the cationic oligomer treatment (Treatment A). The Barnett shale's prevalent damage mechanism in fresh water was decreased permeability in the proppant pack resulting from changes in the confinement of the arrangement. The oligomer treatment Treatment A did not change the damage mechanism; however, with the treatment, the initial conductivity increased, while the damage factor and proppant embedment both decreased. The undamaged surface percentage of the formation increased from 55 to 73%, resulting in a 44% higher initial conductivity. The Mancos shale's damage mechanism in fresh water was predominately attributed to swelling, which caused the fracture width to change −111 μm/1,000 psi. When the oligomer treatment (Treatment A) was used, this decreased to −83 μm/1,000 psi, and the initial conductivity increased 30%. After inclusion of the cationic oligomer treatment (Treatment A), the swelling for Mancos was controlled, and the percentage of proppant embedded more than half a diameter decreased from 26 to 3%; however, the percentage of fines and spalls increased (0 to 26%), indicating the damage mechanism for Mancos changed from swelling to spalling and fines generation after treatment.

Eagle Ford and Marcellus shales originally displayed fluid-induced fines generation, and after the cationic oligomer treatment, their damage mechanisms remained unchanged. The most significant benefits of the treatment were observed in the Eagle Ford shale, with higher initial conductivity (a 39% increase) and lower proppant embedment; however, the stress-induced conductivity loss increased from −350±30 md·ft/1,000 psi to −510±40 md·ft/1,000 psi, and the damage factor was almost the same, from 2.5±0.7 (fresh water) to 2.3±0.8 (after Treatment A) and was still dominated by spalling and fines generation. The Marcellus showed almost no change in conductivity after treatment; the only benefit was a decrease in the percentage of broken proppant, from 24 to 12%. Addition of the treatment decreased the percentage of undamaged surface from 15% with fresh water to 2% with Treatment A. Overall, the small treatment molecule was effective at increasing the initial conductivity for most samples but was not effective at reducing spall formation or fines generation.

Overall, the polymeric material (Treatment B) in the low-permeability shale formation materials decreased the formation of spalls and fines on the surface. Reducing the amount of fines generation improved the proppant pack permeabilities, either by reducing the closure stress effect or by increasing the initial permeability. Permeability attributed to increased closure stress changed for the Barnett and Eagle Ford shales, from −48 and −61 md/1,000 psi in fresh water to −11 and −15 md/1,000 psi with cationic polymer treatment, respectively. The initial proppant pack permeability doubled for Mancos. CT evaluations showed the treatment decreased the fines and spalls by 22% for Eagle Ford and by 47% for Marcellus. Spalling and fines generation only increased for Mancos, which was 0% in fresh water (because the entire surface exhibited swelling) to 19% in the polymeric treatment. Conductivity for Mancos was the highest with the high-molecular-weight cationic polymer treatment, but not all conductivity values increased even though the formation damage decreased for all samples.

Conductivities were the lowest in polymeric treatment fluid (Treatment B) for Barnett and Eagle Ford. The reason the conductivity did not increase as much as expected is because the fluid affects the β-factor from Forcheimer's equation. Further evaluation of the Darcy-Forchheimer equation (Eq. 1 above) includes the β term, which is affected by a frictional coefficient, viscous forces, surface effects, and confinement. When evaluating conductivity based on % Darcy compared to % Forchheimer for fresh water and the small oligomer treatment fluids, the Forchheimer effects were less than 10%, indicating that the β factor was not a significant contributor to conductivity and was therefore negligible. However, for the polymeric treatment, the Forchheimer contribution was more than 20% for some formations, so the frictional, viscous, and confining forces were no longer negligible. Therefore, while the conductivity values decreased in this treatment fluid, the decreases could be attributed to polymeric drag or confinement in the pore spaces, which may affect the fluid's ability to flow through a porous proppant pack; the treatment is still remediating the formation damage attributed to fines generation and spall formation.

Example 3

A workflow according to the present disclosure using conductivity testing, CT imaging, and water analysis and was used to evaluate damage in formation samples from Mancos and Marcellus shale formations in each of deionized (DI) water, a 7% KCl brine, and a treatment fluid comprising 1 gallons per thousand gallons of a small cationic oligomeric stabilization product. Conductivity tests were performed for each of the Mancos and Marcellus using each of the three aforementioned fluids according to the procedures described in Example 1 where the formation wafers were propped with 25-mesh, high-strength proppant, at 2 lbs/ft loading, and were subjected to increasing closure stresses from 2,000-10,000 psi at 250° F. (121° C.).

Figure 9A:
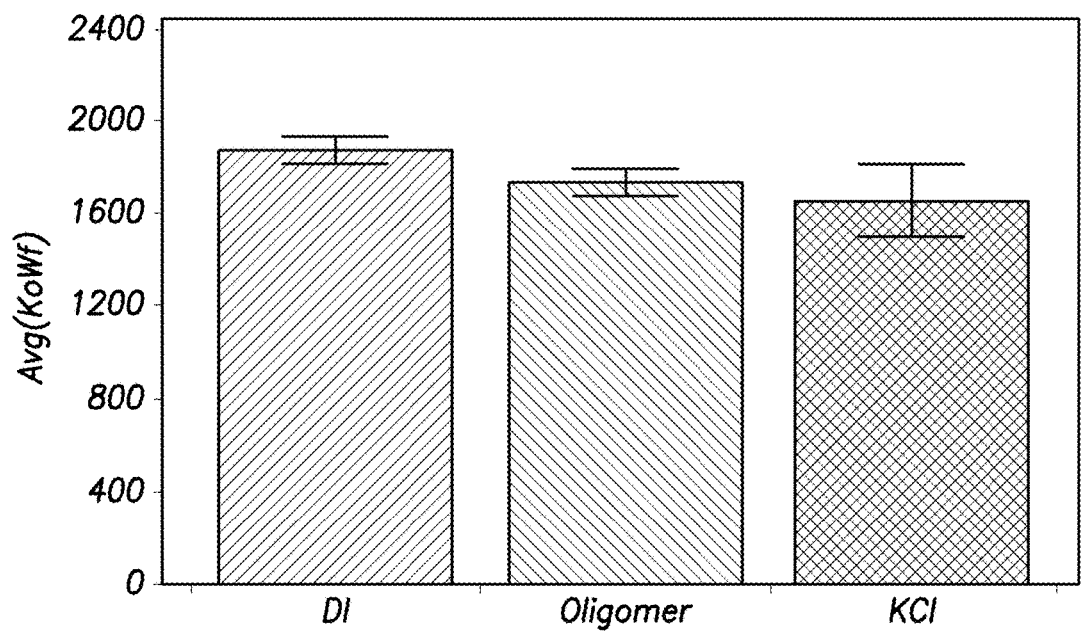
FIGS. 9A and 9B are graphs illustrating data regarding conductivity in certain treated and untreated formation samples according to certain embodiments of the present disclosure.
Figure 9B:
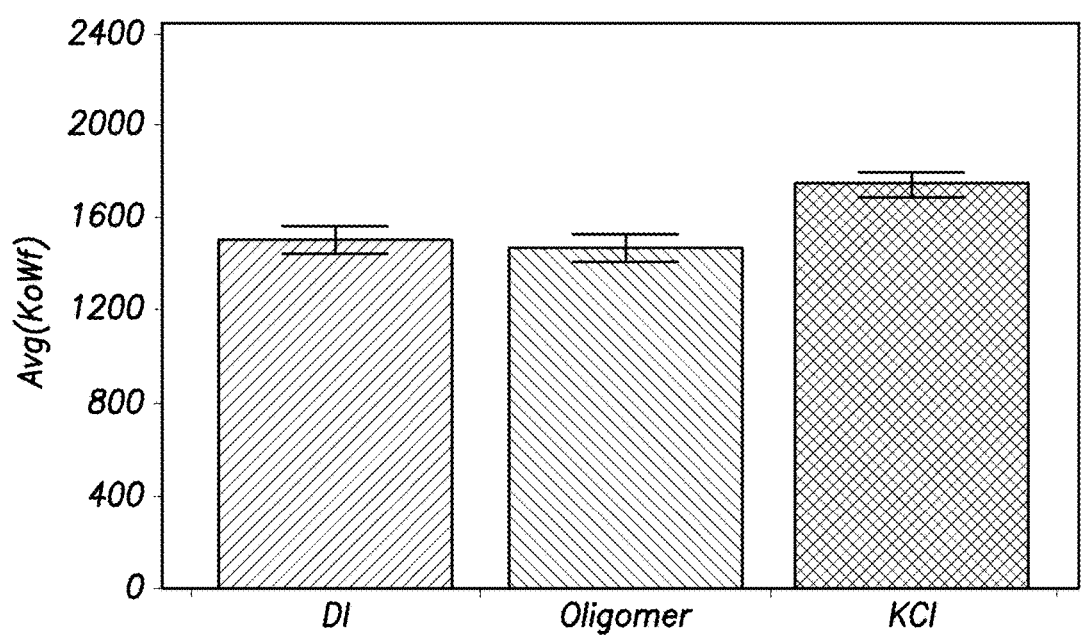

FIGS. 9A and 9B shows the average conductivity over all closure stresses for the Mancos and Marcellus shale formations, respectively, in each fluid. The dotted lines in FIGS. 9A and 9B represent the permeability of the same proppant evaluated in metal cores. As shown, Mancos has an average conductivity in DI water of 1874±60 mD*ft, while the brine and oligomer treatment fluid each have slightly lower conductivity values (oligomer is 1733±57 mD*ft and the brine is 1656±165 mD*ft). For Marcellus, the average conductivity in the DI water and oligomer treatment fluid are almost the same (1458±36, 1430±56 mD*ft, respectively), while the average conductivity for the KCl brine is higher, 1700±42 mD*ft.

Figure 10:
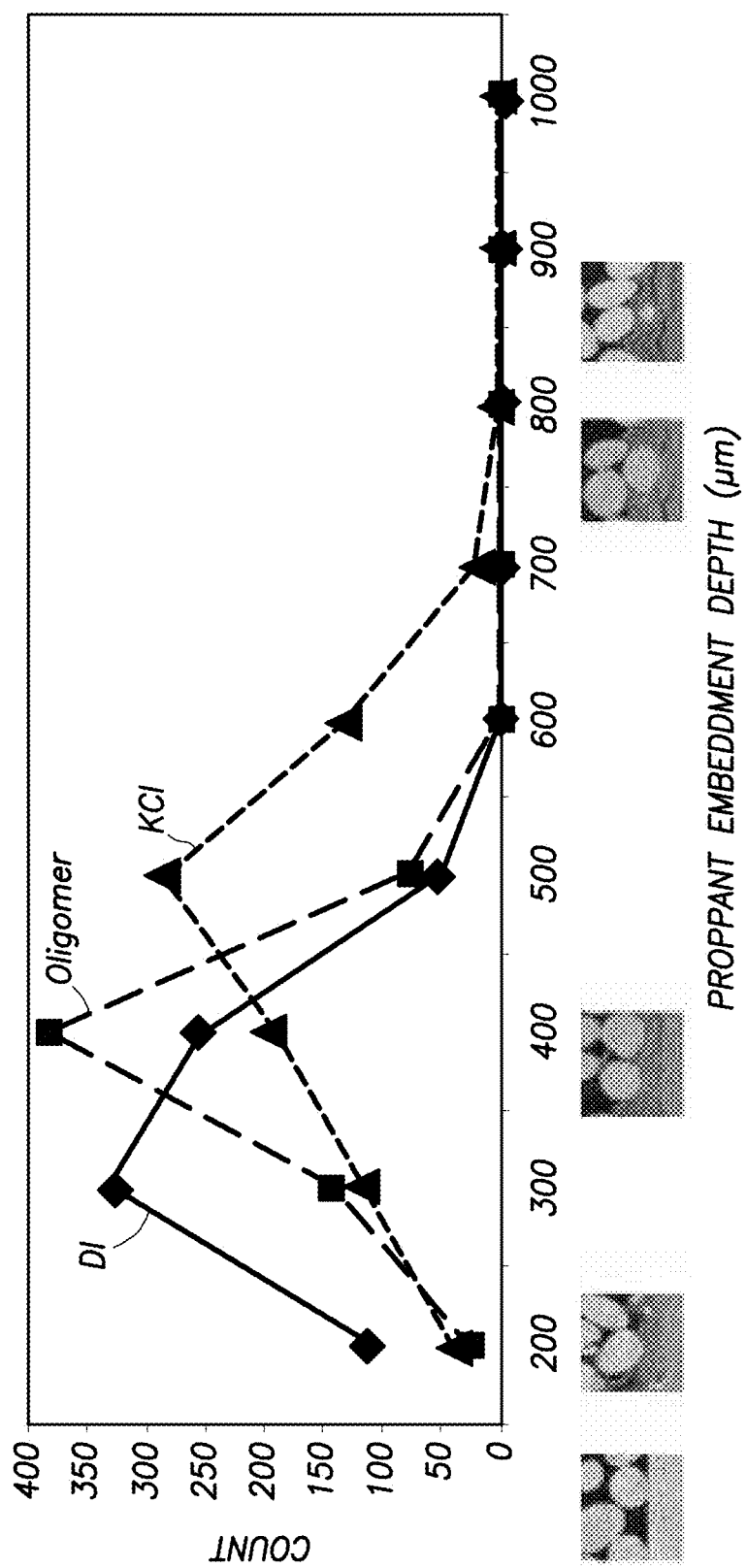
FIG. 10 is a graph illustrating data regarding proppant embedment in certain treated and untreated formation samples according to certain embodiments of the present disclosure.
Figure 11C:
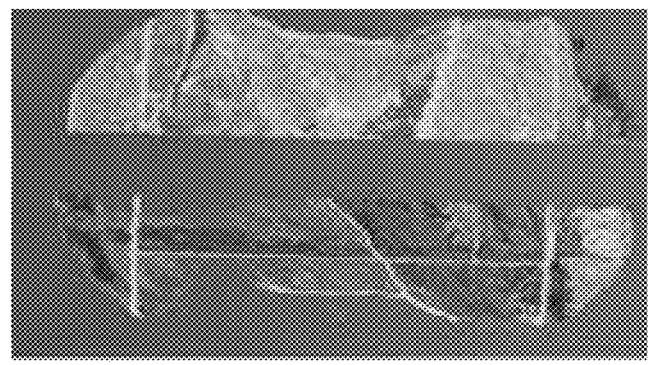
FIGS. 11A, 11B, and 11C are a series of photographic images depicting different degrees of damage in different formations in certain embodiments of the present disclosure.
Figure 11B:
Figure 11A:
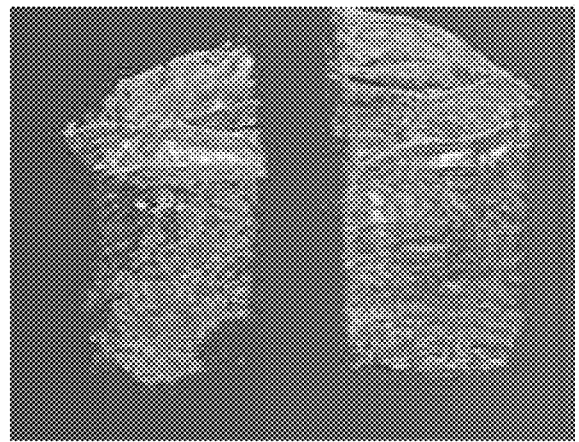
Figure 12:
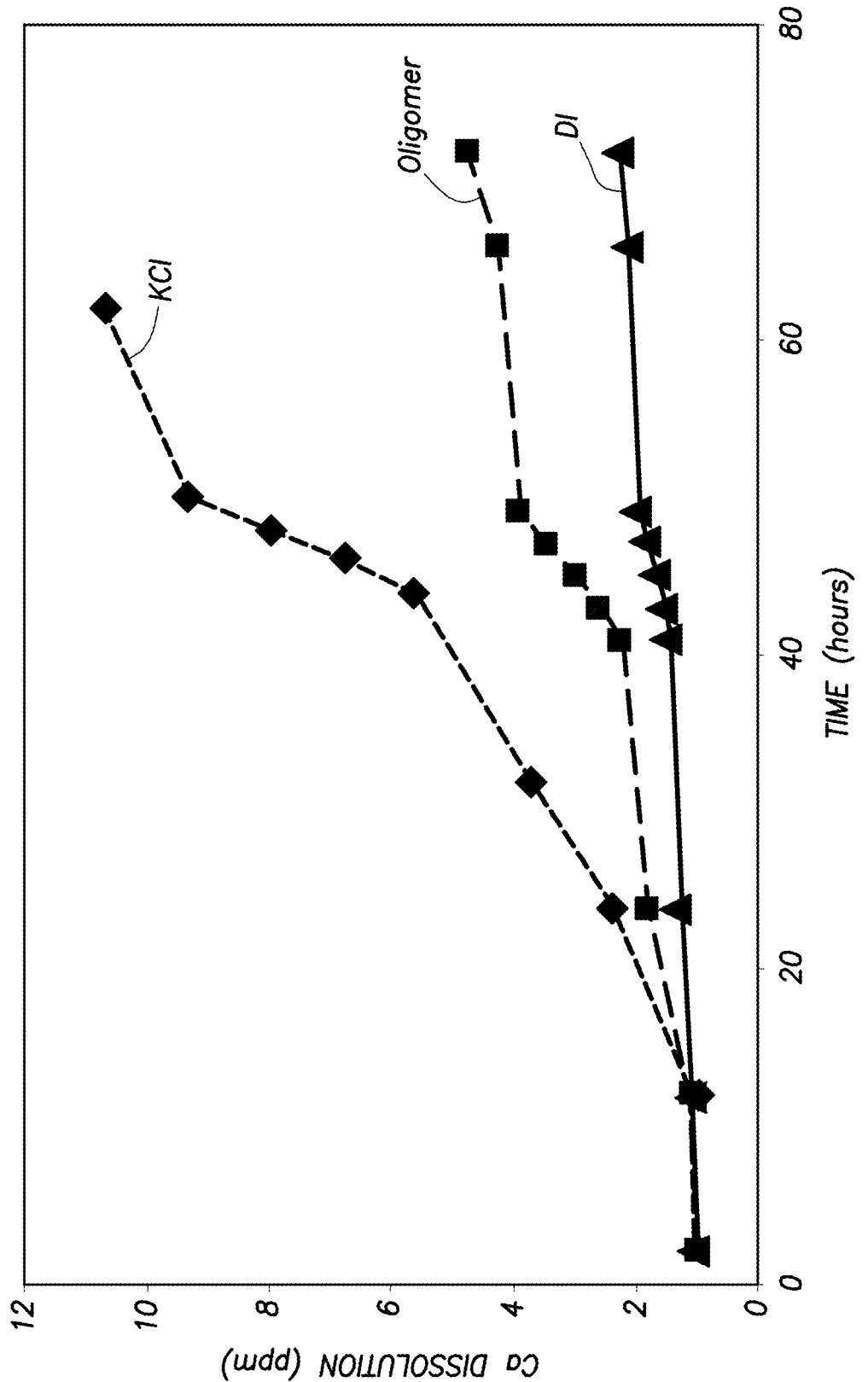
FIGS. 12 and 13 are graphs illustrating data regarding carbonate dissolution in certain treated and untreated formation samples according to certain embodiments of the present disclosure.
Figure 13:
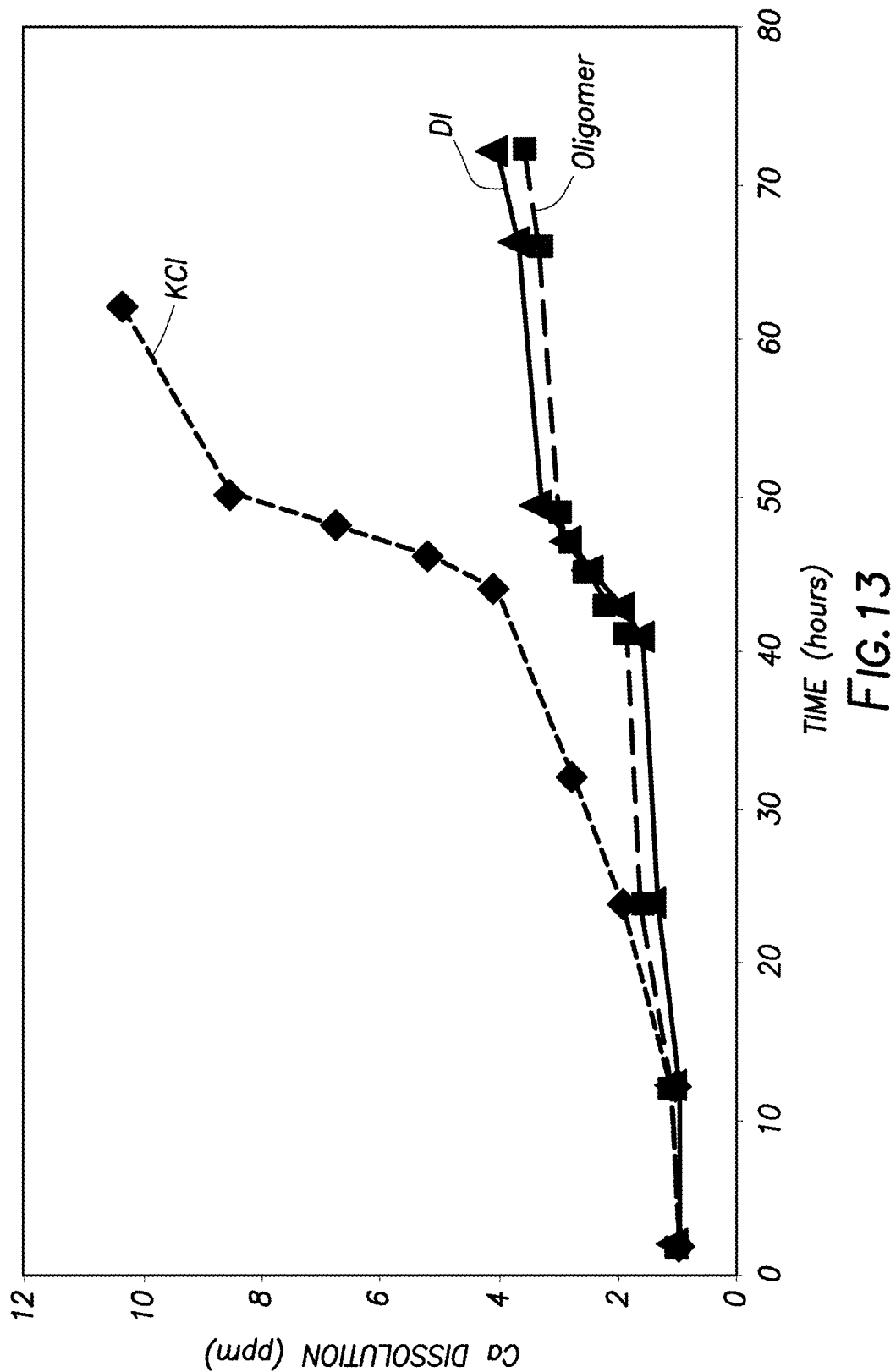

CT imaging was performed on the formation samples from the conductivity testing according to the methods described in Example 1 above. For the Mancos formation, proppant embedment data obtained from analysis of the CT images of each sample is shown in FIG. 10, along with sample images. Images from the samples of Marcellus shale are provided in FIG. 11 (FIG. 11A: sample in DI water; FIG. 11B: sample in oligomer treatment; and FIG. 11C: sample in KCl brine). A water analysis was performed on the effluent from the conductivity testing to evaluate calcium carbonate dissolution for the Mancos and Marcellus formation samples in each fluid, which is plotted in FIGS. 12 (Mancos) and 13 (Marcellus). The carbonate dissolution in each of the oligomer treatment and brine was higher than that in DI water. This finding corresponded well with the CT image analysis. For Mancos, the carbonate concentration is low, and the CT of the Mancos formation samples (thumbnails in FIG. 10) revealed increased swelling distributed randomly throughout the matrix and face and the depth of proppant embedment with increased carbonate dissolution. Marcellus, which has vein rich in carbonate minerals and no major carbonate content in the matrix, showed an alternate effect. The dissolution of carbonate was highest with KCl, and the CT image analysis (FIG. 11) showed that the micro-fracture patterns generated within the wafer were more connected and wider.

In some embodiments, the methods of the present disclosure comprise: subjecting a test formation sample to one or more stress loads, wherein the test formation sample comprises: two wafers of a formation material from a subterranean formation, and a plurality of proppant particulates between and in contact with the two wafers, measuring a conductivity of a test fluid through the test formation sample, wherein an eluted test fluid is collected after passing through the test formation sample; determining one or more damage properties of at least a portion of the test formation sample using computed tomography images of a surface of the test sample; determining one or more properties of the eluted test fluid; and selecting at least one formation stabilization treatment for the subterranean formation based at least in part on one or more of the conductivity of the test fluid through the test formation sample, the damage properties of the test formation sample, and the properties of the eluted test fluid.

In some embodiments, the methods of the present disclosure comprise: measuring a conductivity of water through a first test sample comprising a formation material from a subterranean formation while the first test sample is subjected to one or more stress loads, wherein a first fluid eluted from the first test sample is collected; measuring a conductivity of a treatment fluid through a second test sample comprising the formation material from the subterranean formation while the second test sample is subjected to one or more stress loads, wherein a second fluid eluted from the second test sample is collected; calculating a percent improvement of conductivity through the second test sample as compared to the conductivity through the first test sample; measuring one or more damage properties of at least a portion of the first test sample using computed tomography images of a surface of the first test sample; measuring one or more damage properties of at least a portion of the second test sample using computed tomography images of a surface of the second test sample; calculating a percent improvement of the one or more damage properties of second test sample as compared to the one or more damage properties of the first test sample; measuring one or more properties of at least a portion of the first fluid eluted from the first test sample; measuring one or more properties of at least a portion of the second fluid eluted from the second test sample; calculating a percent improvement of the one or more properties of the second fluid eluted from the second test sample as compared to the one or more properties of the first fluid eluted from the first test sample; and selecting at least one formation stabilization treatment based at least in part on the calculated percent improvements in conductivity of the second test sample, the damage property of the second test sample, and property of the second fluid eluted from the second test sample.

In some embodiments, the methods of the present disclosure comprise: (a) measuring a conductivity of water through a first test sample while the first test sample is subjected to one or more stress loads, wherein the first test sample comprises two wafers of formation material from a subterranean formation and a first plurality of proppant particulates between and in contact with each of the two wafers of formation material, and a first fluid eluted from the first test sample is collected; (b) measuring a conductivity of at least one treatment fluid through at least a second test sample while the second test sample is subjected to one or more stress loads, wherein the second test sample comprises two wafers of formation material from the subterranean formation and a second plurality of proppant particulates distributed between and in contact with each of the two wafers of formation material, and a second fluid eluted from the second test sample is collected; (c) calculating a percent improvement of conductivity through the second test sample as compared to the conductivity through the first test sample; (d) measuring an average proppant embedment depth in at least a portion of the first test sample using computed tomography images of a surface of the first test sample; (e) measuring an average proppant embedment depth at least a portion of the second test sample using computed tomography images of a surface of the second test sample; (f) calculating a percent improvement of the average proppant embedment depth in the second test sample as compared to the average proppant embedment depth in the first test sample; (g) measuring a first amount of carbonate ions dissolved in at least a portion of the first fluid eluted from the first test sample; (h) measuring a second amount of carbonate ions dissolved in at least a portion of the second fluid eluted from the second test sample; (i) calculating a percent reduction of carbonate ions dissolved in the second fluid eluted from the second test sample as compared to the amount of carbonate ions dissolved in the first fluid eluted from the first test sample; and (j) selecting at least one formation stabilization treatment based at least in part on the calculated percent improvements in conductivity of the second test sample, the average proppant embedment depth of the second test sample, and the amount of carbonate ions dissolved in the second fluid eluted from the second test sample.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. While numerous changes may be made by those skilled in the art, such changes are encompassed within the spirit of the subject matter defined by the appended claims. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (e.g., "from about a to about b," or, equivalently, "from approximately a to b," or, equivalently, "from approximately a-b") disclosed herein is to be understood as referring to the power set (the set of all subsets) of the respective range of values. The terms in the claims have their plain, ordinary meaning unless otherwise explicitly and clearly defined by the patentee.

What is claimed is:

1. A method comprising:
    providing a formation material from a subterranean formation:
    subjecting a first test formation sample to one or more stress loads, wherein the first test formation sample comprises:
        two wafers of the formation material, and
        a plurality of proppant particulates between and in contact with the two wafers,
    measuring a conductivity of a test fluid through the first test formation sample, wherein a first eluted fluid is collected after passing through the first test formation sample;
    determining one or more damage properties of at least a portion of the first test formation sample by examining computed tomography images of a surface of the first test formation sample, wherein the one or more damage properties are selected from the group consisting of depth of proppant embedment in the first test formation sample, characteristics of microfractures in the first test formation sample, and any combination thereof;
    determining one or more chemical properties of the first eluted fluid;
    selecting at least a first formation stabilization treatment fluid for the subterranean formation based at least in part on one or more of the conductivity of the test fluid through the first test formation sample, the damage properties of the first test formation sample, and the properties of the first eluted fluids,
    measuring a conductivity of the first formation stabilization treatment fluid through a second test formation sample comprising the formation material from the subterranean formation while the second test formation sample is subjected to one or more stress loads, wherein the second test formation sample comprises
        two wafers of the formation material and
        a plurality of proppant particulates between and in contact with the two wafers, and
    a second fluid eluted from the second test formation sample is collected;
    calculating a percent improvement of conductivity through the second test formation sample as compared to the conductivity through the first test formation sample;
    measuring a conductivity of a second formation stabilization treatment fluid through a third test formation sample comprising the formation material from the subterranean formation while the third test formation sample is subjected to one or more stress loads, wherein the third test formation sample comprises
        two wafers of the formation material, and
        a plurality of proppant particulates between and in contact with the two wafers,
    the second treatment fluid is selected based at least in part on the calculated percent improvements in conductivity of the second test formation sample, the damage property of the first test formation sample, and a property of the first or second fluid eluted from the first or second test formation sample, and
    a third fluid eluted from the third test formation sample is collected; and
    calculating a percent improvement of conductivity through the third test formation sample as compared to the conductivity through the first test formation sample.

2. The method of claim 1 further comprising introducing at least one of the first or second formation stabilization treatment fluid into at least a portion of the subterranean formation.

3. The method of claim 1 wherein the test fluid comprises water.

4. The method of claim 1 wherein the test fluid comprises one or more formation stabilization treatment additives.

5. The method of claim 1 wherein the first or second formation stabilization treatment fluid comprises at least one treatment additive selected from the group consisting of: potassium chloride, sodium chloride, ammonium chloride, tetramethyl ammonium chloride, a cationic polymer, a cationic oligomer, a cationic surfactant, a hydrophobic resin, a transition metal, furfuryl alcohol, ethylene glycol, a quaternary amine, a bisquaternary amine, and any combination thereof.

6. The method of claim 1 wherein the one or more chemical properties of the first eluted fluid comprise at least one property selected from the group consisting of: a turbidity of the fluid, an amount of one or more ionic species dissolved in the fluid, a rate of dissolution of ionic species in the fluid, a pH of the fluid, a viscosity of the fluid, and any combination thereof.

7. The method of claim 1 further comprising:
    analyzing a sample of the formation material from the subterranean formation by performing one or more x-ray diffraction measurements to determine one or more mineralogical properties of the subterranean formation; and
    storing data relating to the one or more mineralogical properties of the subterranean formation and at least one of the first or second selected formation stabilization treatment fluid for the subterranean formation.

8. The method of claim 1 further comprising:
    determining one or more damage properties of at least a portion of the second test formation sample by examining computed tomography images of a surface of the second test formation sample, wherein the one or more damage properties are selected from the group consisting of depth of proppant embedment in the second test formation sample, characteristics of microfractures in the second test formation sample, and any combination thereof; and
    calculating a percent improvement of the one or more damage properties of second test formation sample as compared to the one or more damage properties of the first test formation sample.

9. The method of claim 8 further comprising:
    determining one or more chemical properties of at least a portion of the second fluid eluted from the second test formation sample; and
    calculating a percent improvement of the one or more chemical properties of the second fluid eluted from the second test formation sample as compared to the one or more chemical properties of the fluid eluted from the first test formation sample.

10. The method of claim 9 wherein the one or more chemical properties of the second fluid eluted from the second test formation sample comprises at least one property selected from the group consisting of: a turbidity of the fluid, an amount of one or more ionic species dissolved in the fluid, a rate of dissolution of the ionic species in the fluid, a pH of the fluid, a viscosity of the fluid, and any combination thereof.

* * * * *